(12) United States Patent
Honda

(10) Patent No.: US 9,636,127 B2
(45) Date of Patent: May 2, 2017

(54) METHOD FOR RETRIEVING OBJECTS FROM A LIVING BODY

(71) Applicant: TERUMO KABUSHIKI KAISHA, Tokyo (JP)

(72) Inventor: Kei Honda, Kanagawa (JP)

(73) Assignee: TERUMO KABUSHIKI KAISHA, Shibuya-Ku Tokyo (JP)

( * ) Notice: Subject to any disclaimer, the term of this patent is extended or adjusted under 35 U.S.C. 154(b) by 120 days.

(21) Appl. No.: 14/675,579

(22) Filed: Mar. 31, 2015

(65) Prior Publication Data

US 2016/0287274 A1    Oct. 6, 2016

(51) Int. Cl.
| | |
|---|---|
| A61B 17/221 | (2006.01) |
| A61B 1/00 | (2006.01) |
| A61F 2/01 | (2006.01) |
| A61B 17/22 | (2006.01) |
| A61B 17/00 | (2006.01) |
| A61B 90/00 | (2016.01) |

(52) U.S. Cl.
CPC .............. *A61B 17/221* (2013.01); *A61B 1/00* (2013.01); *A61F 2/01* (2013.01); *A61B 2017/003* (2013.01); *A61B 2017/0034* (2013.01); *A61B 2017/2215* (2013.01); *A61B 2017/22079* (2013.01); *A61B 2090/0811* (2016.02)

(58) Field of Classification Search
CPC ................ A61B 17/22; A61B 17/221; A61B 2017/00292; A61B 2017/00296; A61B 2017/0034; A61B 2017/22038; A61B 2017/22042; A61B 2017/22072; A61B 2017/22074; A61B 2017/22075; A61B 2017/22078; A61B 2017/22079; A61B 2017/22081; A61B 2017/22094; A61B 2017/2215; A61B 2017/2217; A61B 1/005; A61B 1/0051; A61B 1/0055; A61B 1/0056; A61B 1/008; A61B 1/015; A61B 1/018; A61B 1/307
See application file for complete search history.

(56) References Cited

U.S. PATENT DOCUMENTS 4,696,297 A * 9/1987 Pleines .................. A61B 17/22
                                                     606/22
4,784,636 A * 11/1988 Rydell ............. A61B 17/32075
                                                    600/568

(Continued)

OTHER PUBLICATIONS

U.S. Appl. No. 14/222,021, filed Mar. 21, 2014, Kei Honda.
U.S. Appl. No. 14/221,954, filed Mar. 21, 2014, Kei Honda.
U.S. Appl. No. 14/221,858, filed Mar. 21, 2014, Kei Honda.

*Primary Examiner* — Ryan J Severson
(74) *Attorney, Agent, or Firm* — Buchanan Ingersoll & Rooney PC

(57) ABSTRACT

A method of moving a device toward a target site in a living body involves introducing an endoscope into the living body, wherein the endoscope has an instrument channel, with the device located at the distal end of the endoscope, and an elongated shaft connected to the device and positioned in the instrument channel. The method includes moving the endoscope and the device within the living body toward the target site, changing the shape of the elongated shaft while moving the device in the living body, and moving the device within the living body while the device is in the second orientation to position the device in the second orientation at the target site.

20 Claims, 14 Drawing Sheets

(56) References Cited

U.S. PATENT DOCUMENTS

| | | | | |
|---|---|---|---|---|
| 4,926,858 A * | 5/1990 | Gifford, III | A61B 17/22031 | 604/22 |
| 5,085,662 A * | 2/1992 | Willard | A61B 17/22012 | 606/159 |
| 5,423,838 A * | 6/1995 | Willard | A61B 17/22012 | 600/439 |
| 5,989,266 A * | 11/1999 | Foster | A61B 17/221 | 606/114 |
| 6,174,307 B1 * | 1/2001 | Daniel | A61B 1/00098 | 600/103 |
| 6,238,401 B1 * | 5/2001 | Richter | A61B 1/00147 | 128/898 |
| 6,258,083 B1 * | 7/2001 | Daniel | A61B 1/00098 | 606/15 |
| 6,544,227 B2 * | 4/2003 | Sahatjian | A61B 17/22012 | 604/113 |
| 6,565,530 B2 * | 5/2003 | Sahatjian | A61B 17/22012 | 604/113 |
| 6,663,594 B2 * | 12/2003 | Sahatjian | A61B 17/22012 | 604/113 |
| 6,692,484 B1 * | 2/2004 | Karpiel | A61B 17/22031 | 600/31 |
| 6,866,651 B2 * | 3/2005 | Constantz | A61B 17/22 | 514/891 |
| 7,101,379 B2 * | 9/2006 | Gregory, Jr. | A61B 17/221 | 606/127 |
| 7,137,966 B2 * | 11/2006 | Sahatjian | A61B 17/22012 | 604/113 |
| RE40,305 E * | 5/2008 | Richter | A61B 1/00147 | 128/898 |
| 7,582,054 B2 * | 9/2009 | Okada | A61B 1/00133 | 600/104 |
| 7,731,722 B2 * | 6/2010 | Lavelle | A61B 17/221 | 606/127 |
| 7,837,672 B2 * | 11/2010 | Intoccia | A61B 17/22 | 604/101.01 |
| 7,906,152 B2 * | 3/2011 | Constantz | A61B 17/22 | 424/666 |
| 7,946,978 B2 * | 5/2011 | Okada | A61B 1/00133 | 600/104 |
| 7,963,944 B2 * | 6/2011 | Sahatjian | A61B 17/22012 | 604/113 |
| 8,197,463 B2 * | 6/2012 | Intoccia | A61B 17/22 | 604/101.01 |
| 8,372,037 B2 * | 2/2013 | Sahatjian | A61B 17/22012 | 604/113 |
| 8,394,059 B2 * | 3/2013 | Sahatjian | A61B 17/22012 | 604/113 |
| 8,409,218 B2 * | 4/2013 | Schwarz | A61B 17/12022 | 600/420 |
| 8,409,237 B2 * | 4/2013 | Galdonik | A61B 17/22 | 606/200 |
| 8,679,059 B2 * | 3/2014 | Sahatjian | A61B 17/22012 | 604/113 |
| 8,834,416 B2 * | 9/2014 | Sahatjian | A61B 17/22012 | 604/113 |
| 8,998,928 B2 * | 4/2015 | Schwarz | A61B 17/12022 | 600/430 |
| 2001/0025174 A1 * | 9/2001 | Daniel | A61B 1/00098 | 606/15 |
| 2002/0119116 A1 * | 8/2002 | Sahatjian | A61B 17/22012 | 424/78.31 |
| 2002/0120237 A1 * | 8/2002 | Sahatjian | A61B 17/22012 | 604/180 |
| 2003/0088254 A1 * | 5/2003 | Gregory, Jr. | A61B 17/221 | 606/127 |
| 2003/0178030 A1 * | 9/2003 | Constantz | A61B 17/22 | 128/898 |
| 2003/0195464 A1 * | 10/2003 | Sahatjian | A61B 17/22012 | 604/113 |
| 2003/0229332 A1 * | 12/2003 | Intoccia | A61B 17/22 | 604/508 |
| 2004/0019358 A1 * | 1/2004 | Kear | A61B 17/22031 | 606/127 |
| 2005/0043756 A1 * | 2/2005 | Lavelle | A61B 17/221 | 606/200 |
| 2005/0053662 A1 * | 3/2005 | Sahatjian | A61B 17/22012 | 424/486 |
| 2005/0119522 A1 * | 6/2005 | Okada | A61B 1/00133 | 600/106 |
| 2005/0143678 A1 * | 6/2005 | Schwarz | A61B 17/12022 | 601/4 |
| 2005/0251104 A1 * | 11/2005 | Constantz | A61B 17/22 | 604/514 |
| 2005/0277976 A1 * | 12/2005 | Galdonik | A61B 17/22 | 606/200 |
| 2006/0189921 A1 * | 8/2006 | Galdonik | A61B 17/22 | 604/27 |
| 2006/0233891 A1 * | 10/2006 | Constantz | A61B 17/22 | 424/666 |
| 2007/0066933 A1 * | 3/2007 | Sahatjian | A61B 17/22012 | 604/23 |
| 2007/0088256 A1 * | 4/2007 | Intoccia | A61B 17/22 | 604/102.02 |
| 2008/0015410 A1 * | 1/2008 | Okada | A61B 1/00133 | 600/107 |
| 2008/0103481 A1 * | 5/2008 | Vogel | A61B 17/12022 | 604/514 |
| 2008/0188866 A1 * | 8/2008 | Karpiel | A61B 17/22032 | 606/127 |
| 2010/0274231 A1 * | 10/2010 | Pravong | A61B 17/22 | 606/2.5 |
| 2011/0060256 A1 * | 3/2011 | Schwarz | A61B 17/12022 | 601/4 |
| 2011/0092957 A1 * | 4/2011 | Intoccia | A61B 17/22 | 604/540 |
| 2011/0245801 A1 * | 10/2011 | Sahatjian | A61B 17/22012 | 604/506 |
| 2012/0010595 A1 * | 1/2012 | Sahatjian | A61B 17/22012 | 604/506 |
| 2013/0131445 A1 * | 5/2013 | Zerfas | A61B 17/22 | 600/104 |
| 2013/0150789 A1 * | 6/2013 | Sahatjian | A61B 17/22012 | 604/131 |
| 2013/0172789 A1 * | 7/2013 | Schwarz | A61B 17/12022 | 601/4 |
| 2013/0231676 A1 * | 9/2013 | Sahatjian | A61B 17/22012 | 606/127 |
| 2015/0265294 A1 * | 9/2015 | Honda | A61B 17/22 | 606/128 |
| 2015/0265295 A1 * | 9/2015 | Honda | A61B 17/22 | 606/127 |
| 2015/0265296 A1 * | 9/2015 | Honda | A61B 17/22 | 606/127 |
| 2015/0265297 A1 * | 9/2015 | Honda | A61B 17/22 | 606/127 |
| 2015/0265298 A1 * | 9/2015 | Honda | A61B 17/22 | 606/127 |
| 2016/0015393 A1 * | 1/2016 | Schwarz | A61B 17/12022 | 601/4 |
| 2016/0081701 A1 * | 3/2016 | Honda | A61B 17/221 | 606/127 |
| 2016/0081703 A1 * | 3/2016 | Honda | A61B 17/22031 | 606/127 |
| 2016/0089171 A1 * | 3/2016 | Honda | A61B 17/22 | 606/128 |
| 2016/0089173 A1 * | 3/2016 | Honda | A61B 17/22031 | 606/127 |
| 2016/0089174 A1 * | 3/2016 | Honda | A61B 17/22031 | 606/127 |
| 2016/0089185 A1 * | 3/2016 | Honda | A61B 17/50 | 606/127 |

* cited by examiner

METHOD FOR RETRIEVING OBJECTS FROM A LIVING BODY

CROSS-REFERENCE TO OTHER APPLICATIONS

This application discloses subject matter related to subject matter described in U.S. application Ser. No. 14/222,021, U.S. application Ser. No. 14/221,954 and U.S. application Ser. No. 14/221,858, the entire content of each of which is incorporated herein by reference.

TECHNICAL FIELD

The present invention generally pertains to methods and systems for retrieving/removing a mass from a human body. More specifically, the invention involves methods and systems for retrieving/removing stone(s) (e.g., calculus or calculi) from a portion of a human body such as the renal pelvis or the ureter.

BACKGROUND DISCUSSION

The term urinary calculus/Calculi (e.g., kidney stone(s) and ureteral stone(s)) refers to mass(es) or stone(s), typically solid particle(s), that form in the human body and is located in the kidney and/or the ureter. They can exhibit a variety of chemical compositions including calcium oxalate, calcium phosphate, uric acid, cystine, and struvite.

Stone disease (e.g., kidney stones and ureteral stones) is a relatively common urological disorder. The presence of calculus in the body can manifest itself in a variety of ways and can produce a number of medical ailments. For example, the presence of calculus in the renal pelvis and/or the renal calix (i.e., the lumen of the kidney) can cause blood in the urine, urinary obstruction, infection, and various degrees of pain ranging from vague frank pain to much more severe pain not capable of being relieved through general pain medication. The presence of stones or calculi in the ureter can result in relatively severe side and back pain, pain below the ribs, and pain that sometimes spreads to the lower abdomen and groin, as well as pain during urination and hematuria.

Fortunately, many calculi or stones pass out of the body without requiring any specific medical intervention. In those situations where the calculus does not naturally pass out of the body, a medical procedure may be required. Known medical procedures typically fall into three categories.

In the past, three main treatments have been used to address calculus or kidney stones. These include shock wave lithotripsy (ESWL), transurethral lithotripsy or ureteroscopy (URS), and percutaneous nephrouretero lithotripsy (PCNL) which is sometimes also referred to as percutaneous nephrolithotomy (PCN).

Shock wave lithotripsy is performed as an extracorporeal treatment. This treatment utilizes a machine called a lithotripter that operates by directing ultrasonic or shock waves from outside the body, through the skin and tissue, and at the calculi or stones. Repeated shock waves apply stress to the stones, eventually breaking the individual stones into smaller pieces which can more easily pass through the urinary tract in urine. One benefit associated with shock wave lithotripsy is that it is a rather simple procedure. But it has been found that there is a relatively high rate of kidney stone recurrence following shock wave lithotripsy.

Transurethral lithotripsy or ureteroscopy represents one such alternative form of treatment. This treatment involves the use of small fiber optic instrument (endoscope) called an ureteroscope which allows access to the calculus in the ureter or kidney. The ureteroscope can be a rigid ureteroscope or more commonly, a flexible ureteroscope. The ureteroscope allows the medical professional to visualize the stone as the ureteroscope moves along the ureter or enters the kidney by way of the bladder and the urethra. Once the calculus is visualized, a basket-like device is used to grasp smaller stones and remove them. If the calculus is excessively large to remove as a single piece, it can be broken into smaller pieces by using laser energy.

The third form of treatment is percutaneous nephrolithotomy. This procedure is often used with relatively larger calculus that cannot be effectively treated with either ESWL or URS. Percutaneous nephrolithotomy involves nephrostomy; making an incision at the appropriate location, needling by paracentesis needle, positioning a guide wire through the paracentesis needle's lumen into the kidney under radiographic guidance, and then expanding perforated site. A nephroscope is then moved into the kidney via nephrostomy to visualize the calculus. Fragmentation of the calculus can be performed using an ultrasonic probe or laser.

Though these procedures have been commonly used, they are susceptible of certain short comings. For example, the ESWL procedure results in a relative large number of small calculi or small stones, while other procedures require a relatively narrow and long access route or are difficult to implement due to the inability to accurately capture the stones. In addition to, many crush pieces should be removed one by one in URS and PCNL procedure. The procedure time can also be excessively long, and can result in a relatively low "stone free rate." The recurrence rate can also be unacceptably high. And the potential patient complications (e.g., ischemia of the ureter, obstruction of ureter, back-flow and/or high-stress to the renal pelvis, infection of the urinary tract, and other possible injury) can be undesirably high.

Instances also arise, when performing procedures to gain access to calculus, as well as other procedures not specifically involving calculus, where it is desirable or necessary to advance a device into a narrow region in the living body or along an extremely curved path in the living body. The operational procedure can be performed using endoscope (ureteroscope), where the device is positioned in the instrument channel of the endoscope. The device and the endoscope tend to be rather rigid and thus not well suited to being advanced into a narrow region in the living body or moved along an extremely curved path in the living body.

SUMMARY

One aspect of the disclosure here involves a method of moving a device toward a target site in a living body. The method includes introducing an endoscope into the living body, wherein the endoscope possesses a distal end and an instrument channel extending along the longitudinal extent of the endoscope and opening adjacent the distal end of the endoscope. A device is located at the distal end of the endoscope, with an elongated shaft connected to the device and positioned in the instrument channel. The device and the endoscope are movable together, and the introduction of the endoscope into the living body also introduces the device into the living body. The method additionally involves moving the endoscope and the device within the living body toward the target site, changing the shape of the elongated shaft while moving the device in the living body so that an angular orientation of the device relative to a distal end of the elongated shaft changes from a first angular orientation to a second angular orientation, maintaining a shape of the elongated shaft unless an external force is applied to the elongated shaft, with the second angular orientation being different from the first angular orientation, and moving the device within the living body toward the target site while the device is in the second angular orientation to position the device at the target site.

In accordance with another aspect, a method of moving a device toward a target site in a living body involves changing the shape of an elongated shaft that is connected to a device, wherein the device is located at a distal end of an endoscope, and the endoscope includes an instrument channel extending along a longitudinal extent of the endoscope and opening adjacent the distal end of the endoscope, with the elongated shaft being positioned in the instrument channel. The shape of the elongated shaft is changed from a first shape to a second bent shape by applying a force that changes the shape of the elongated shaft, with the elongated shaft maintaining the second shape after removing the force. The method further includes introducing the endoscope together with the elongated shaft and the device into a lumen in the living body to cause the elongated shaft in the second bent shape to straighten from the second bent shape toward the first shape, moving the endoscope together with the elongated shaft and the device along the lumen in the living body toward the target site, restoring the elongated shaft toward the second bent shape when the elongated shaft reaches an enlarged region in the living body, viewing an indicator at a proximal surface of the device to identify a change from the first bent shape to the second bent shape, wherein the indicator is viewed by a viewing system in the endoscope, moving the device and the elongated shaft which has been restored toward its second bent shape in an insertion direction toward the target sit, and positioning the endoscope together with the device and the elongated shaft which has been restored toward its second bent shape at the target site.

An additional aspect of the disclosure here involves a method of moving a device toward a target site in a living body, wherein the method comprises introducing an endoscope into the living body, wherein the endoscope possesses a distal end and an instrument channel extending along a longitudinal extent of the endoscope and opening adjacent the distal end of the endoscope, with a device located at the distal end of the endoscope and possessing a central axis, and an elongated shaft possessing a distal end portion connected to the device and positioned in the instrument channel. The device is rotatable about a hinge, the device and the endoscope are movable together, and the introduction of the endoscope into the living body also introducing the device into the living body. The method also includes moving the endoscope and the device within the living body toward the target site, rotating the device about the hinge to change the angular orientation of the device relative to the shaft from a first angular orientation in which the angle between the central axis of the distal end portion of the elongated shaft and the central axis of the device is a first angle to a second angular orientation in which the angle between the central axis of the distal end portion of the elongated shaft and the central axis of the device is a second angle that is different from the first angle. The device is moved within the living body while the device is in the second angular orientation to position the device at the target site.

Other features and aspects of the calculus retrieving methods and devices disclosed here will become more apparent from the following detailed description considered with reference to the accompanying drawing figures in which like elements are designated by like reference numerals.

DETAILED DESCRIPTION

Set forth below is a detailed description of features and aspects of the retrieving system, device and operational procedure or method described here as examples of the disclosed invention. The systems, devices and operational procedures disclosed here for retrieving calculus have useful application to retrieve calculus/calculi located in the living body, including calculus/calculi located in the kidneys (kidney stones). The references below to calculus should be understood to refer to calculus in the singular as well as calculi in the plural. It is also to be understood that the methods, systems and devices disclosed here are not limited to retrieving calculus in a living body.

Generally speaking, the calculus retrieving device disclosed here, as represented by the several embodiments representing examples of the inventive retrieving device (and method), is configured to be positioned inside a living body at a position which will allow the retrieving device to suck-in or draw-in calculus to be retrieved. Set forth below is a detailed description of features and aspects of the calculus retrieving system, including a calculus retrieving device, and method described here by way of various embodiments representing examples of the disclosed inventions. The systems, devices and methods or operational procedures disclosed here for retrieving calculus have particular useful application to retrieve calculus located at places in the human body where removal of the calculus may otherwise be difficult due to, for example, the need to traverse a rather sharp curve to access the target site and/or the need to enter a rather narrow region to move toward and reach the target site.

Generally speaking, the calculus retrieving device disclosed here, as characterized by the several embodiments representing examples of the inventive calculus retrieving device (and method), is configured to be positioned inside a living body, at a position adjacent the location of calculus to be retrieved from the living body. The calculus (stone/stones) is drawn towards the retrieving device by creating a suction force in the retrieving device. After the calculus is retrieved, the calculus is retained or held by the retrieving device. The retrieving device can then be moved to the new location in the living body at which the retrieved calculus is to be repositioned. The retained calculus is subsequently released at the new location in the living body. Appropriate procedures (e.g., lithotripsy) can then be performed with respect to the calculus which has been moved. Alternatively, the retained calculus can be subsequently removed from the living body.

Figure 1:
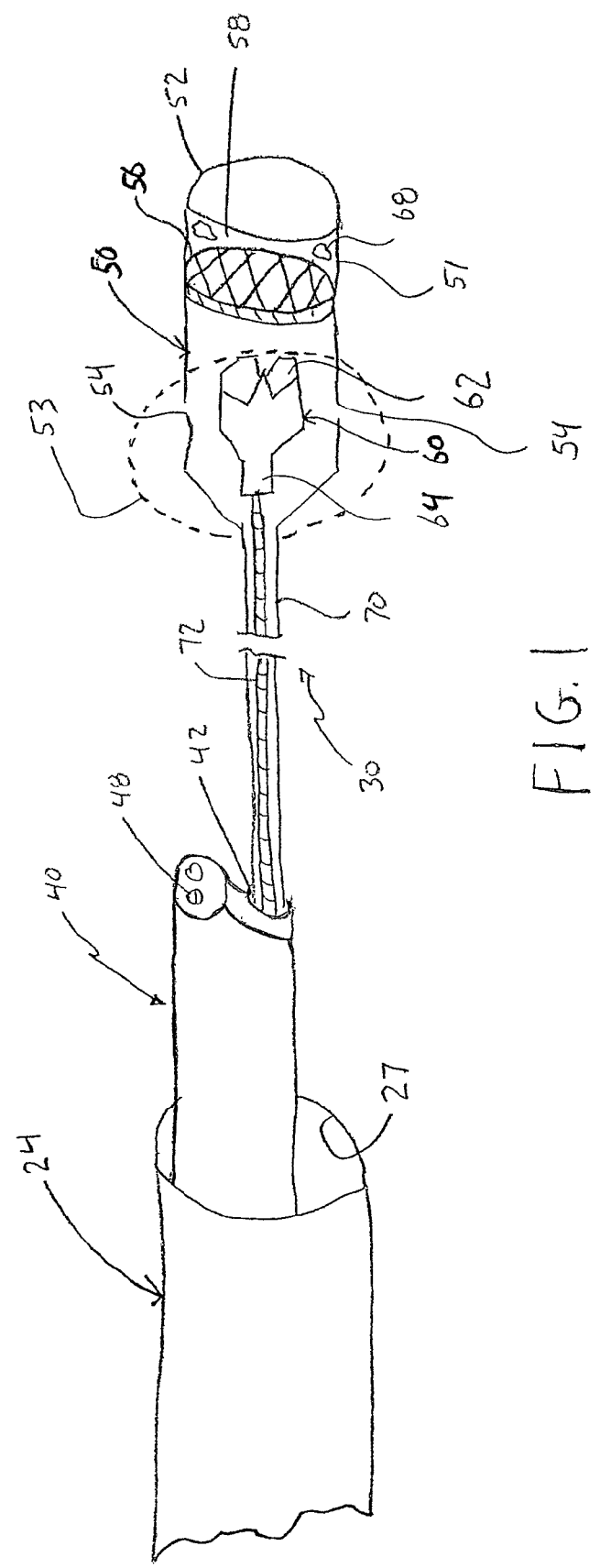
FIG. 1 is a schematic illustration of a system useful to retrieve calculus/calculi, including a retrieving device connected to an operation member (not shown in FIG. 1) through the intermediary of a lumen in an elongated body.

Turning now to the drawing figures, FIG. 1 illustrates, in a schematic fashion, a system 20 for retrieving and moving (removing) calculus (stone or stones) located in a living body. The system 20 includes a retrieving device 30 and an elongated body 40 possessing a lumen to deliver the retrieving device 30 to the desired place in the living body. In this illustrated embodiment representing one example of the system disclosed here, the elongated body 40 is an endoscope, particularly an ureteroscope. The endoscope or ureteroscope 40 includes a lumen or instrument channel 42, which receives a portion of the retrieving device 30, as will be described in more detail below. During use of the retrieving device 30, the ureteroscope 40 is introduced into the living body by way of a ureteral access sheath 24. The ureteroscope 40 passes through a lumen 27 in the ureteral access sheath 24.

Figure 3:
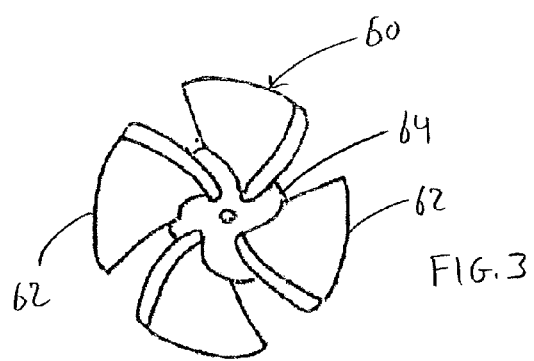
FIG. 3 is a front view of the impeller forming a part of the retrieving device shown in FIG. 2.
Figure 2:
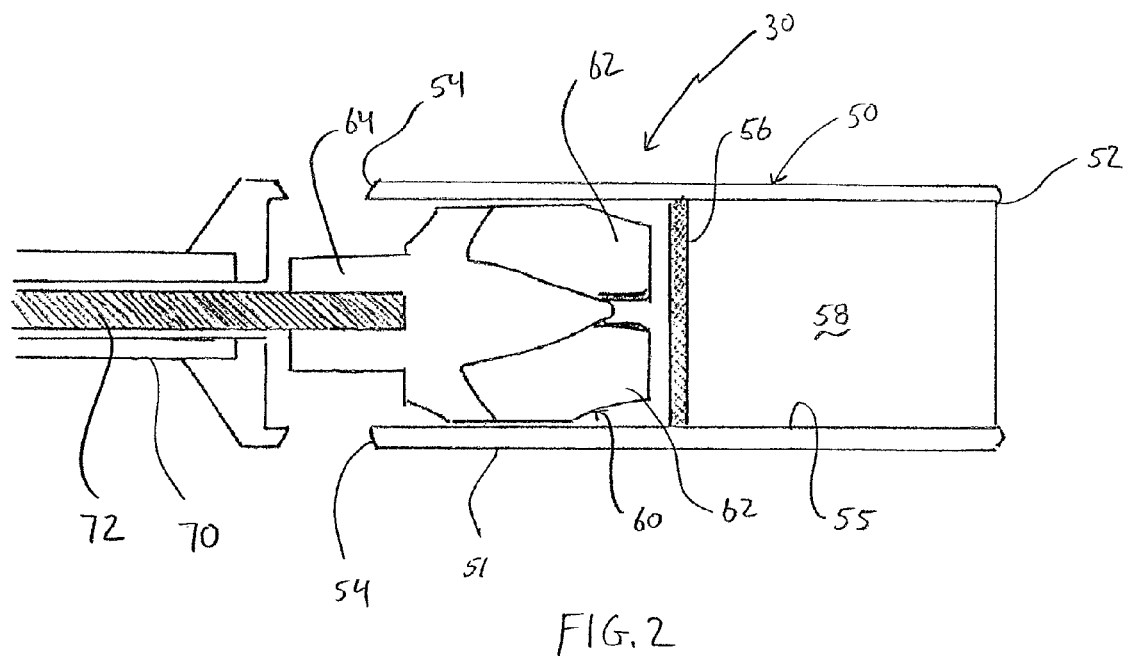
FIG. 2 is a side view, partially in cross section, of a retrieving device according to an embodiment representing an example of the retrieving device disclosed here.

Additional details and features associated with the calculus retrieving device 30 can be seen with reference to FIGS. 1, 2 and 3. The calculus retrieving device 30 includes a suction head 50 comprised of an elongated body or housing 51 having an open distal end 52. The housing 51 is a tubular housing possessing a lumen 54 defining an interior of the housing 51. The housing 51 can be configured as a cylindrical elongated body or housing.

The retrieving device 30 also includes a rotatable suction-producing part located inside the housing 51. In the illustrated embodiment, the rotatable suction-producing part is in the form of an impeller 60. As shown in FIGS. 1 and 3, the impeller is positioned in the housing 51 at a location spaced away from (i.e., proximally or rearwardly) the open distal end 52. An example of the impeller 60 is illustrated in FIG. 3. The impeller 60 includes a plurality of circumferentially spaced apart fins or blades 62 that are fixed to a central hub 64. The fins or blades 62 of the impeller 60 may be twisted fins or blades. The hub 64 is fixed or connected to a rotatably driven drive shaft 72 (a drive shaft) forming part of the device so that the drive shaft 72 and the impeller 60 rotate together as a unit. The impeller 60 is configured so that rotation of the impeller 60 in one rotational direction produces suction in the lumen 54 (in the interior) of the housing 51, while rotation of the impeller 60 in the opposite rotational direction produces the opposite result, namely an outwardly directed force out of the lumen 54. The blades 62 of the impeller 60 shown in FIGS. 2 and 3 are preferably twisted from the distal tip of the blades 62 (radially outermost tip of the blades) toward the bottom portion of the impeller where the blades are mounted. When the direction of the impeller rotation is the same as the twist direction of the blades 62, a suction force is generated. This direction of rotation of the impeller is referred to as overspin direction.

The drive shaft 72 that is connected to the hub 64 of the impeller 60 is positioned inside a shaft cover 70 and is covered by the shaft cover 70 which forms part of the device. In the illustrated embodiment, the drive shaft 72 is completely covered by the shaft cover 70. The shaft cover 70 is fixed to the housing 51 forming the suction head 50 so that movement of the shaft cover 70 results in movement of the suction head 50 (including the housing 51 and the impeller 60).

The housing 51 forming the suction head 50 includes a plurality of circumferentially spaced apart openings or through holes 54. These openings or through holes 54 are positioned closer to the proximal end of the housing 51 than the distal end of the housing 51. These openings or through holes 54 form an exhaust path during operation of the retrieving device, as will become more apparent from the description below. That is, liquid (e.g., water) which has been drawn into the housing 51 of the suction head 50 during operation of the retrieving device 30 is exhausted or discharged out of the suction head 50 by way of the openings or through holes 54.

The suction head 50 further includes a filter 56 located inside the housing 51 at a position between the distal end of the impeller 60 and the open distal end 52 of the suction head 50. This filter 56 is a disc-shaped mesh member that allows the passage of fluid (e.g., liquid such as water), while also preventing the passage of calculus which has been retrieved through operation of the retrieving device 30. The filter 56 possesses an outer periphery (outer circumferential surface) in contact with the inner periphery of the suction head 50. The filter 56 is positionally fixed within the interior of the housing 51 forming the suction head 50.

The suction head 50 also includes a retrieval space 58 located between the filter 56 and the open distal end 52 of the housing 51. As will be described in more detail below, this retrieval space 58 is configured to receive calculus which has been retrieved as a result of the operation of the retrieving device 30.

During operation of the retrieving device 30, the suction head 50 is located at a position in a living body to retrieve calculus. That is, the suction head 50 is positioned relative to the calculus to be retrieved such that during operation of the retrieving device 30, the calculus will be drawn towards (sucked towards) the suction head 50. When the suction head 50 is properly positioned relative to the calculus to be retrieved, the impeller 60 is rotatably driven through operation of a drive device connected to the drive shaft 72. The drive device rotates the drive shaft 72, which in turn rotates the impeller 60. The impeller 60 is rotatably driven in a direction to create suction in the interior of the housing 51 that draws calculus toward the open distal end 52 of the suction head 50. The suction force created by the rotation of the impeller 60 draws relatively smaller calculus (schematically shown in FIG. 1 and identified as 68) through the open distal end 52 of the suction head and into the retrieval space 58 in the housing 51. The suction force created by the rotation of the impeller 60 can also draws relatively larger calculus into contact with the distal end of the suction head 50. That is, calculus possessing an outer dimension larger than the size of the open distal end 52 of the suction head 50 can nevertheless be drawn towards the suction head 50 and retained by the suction head 50 by creating sufficient suction force in the interior of the housing 51 that holds the relatively larger calculus in contact with the distal end of the suction head 50.

Thus, by positioning the suction head 50 in the living body so that the open distal end 52 of the suction head 50 is located at a position that will allow the calculus (i.e., calculus to be retrieved) to be drawn-into or sucked into the retrieval space 58 upon rotational operation of the impeller 60, it is possible to retrieve calculus and hold the retrieved calculus either in the retrieval space 58 or at the distal end of the suction head 50. As the impeller 60 is rotated to draw calculus toward the suction head 50, liquid (e.g., water) is drawn into the retrieval space 58 by way of the distal open end 52 of the suction head 50. This liquid is passes through the filter 56, and is exhausted or discharged outside the housing 51 of the suction head 50 through the openings or through holes 54. On the other hand, the filter 56 is sized to ensure that calculus which is drawn into the retrieval space 58 of the suction head 50, does not pass through the filter 56. The rotational operation of the impeller 60 thus causes liquid flow in which liquid enters the distal open end 52 of the suction head 50, passes through the filter 56, and exits through the through holes or openings 54 in the suction head 50. Depending upon operation of the impeller 60, the liquid exhausted through the openings or through holes 54 can also be at least partially drawn back into the interior of the suction head 50, thus creating a rather turbulent and continuous liquid cycle in which the same liquid is repeatedly drawn into the suction head, exhausted through the suction head 50, drawn into the suction head, etc. This turbulent and continuous liquid cycle can help facilitate retrieval of calculus in the retrieval space 58 of the suction head 50. This is because the suction force per rotation of the impeller is increased. In addition, the calculus tends to float, making it easier to draw-in or retrieve the calculus. When drawing-in calculus in a narrow lumen in a living body (e.g. ureter), the continuous liquid cycle helps prevent fluid surrounding calculus from drying up.

Set forth next is a description of ways in which the system for retrieving calculus disclosed here can be used, as well as a description of operational procedures performed using the calculus retrieving system. Calculus that is not excessively large can be retrieved and removed from the living body using the retrieving system, device and operational procedures or methods disclosed here. But it is sometimes necessary or desirable to break-up calculus located in a living body. For instance, if the calculus is relatively large (e.g., larger than the ureter diameter), it is not possible to remove the calculus from the living body. In such situations, it would be desirable to break-up the calculus into smaller size pieces. This can oftentimes be accomplished using lithotripsy. Circumstances may make it difficult to perform lithotripsy to break-up calculus in the living body. For example, the calculus may be located at a place where damaged tissue exists, for example in a portion of the ureter in which there is damaged tissue. Alternatively, the calculus may be located in a portion of the living body (e.g., ureter) that is rather small in size (i.e., a narrow space) and difficult to access with appropriate instrumentation and equipment for performing lithotripsy (e.g., a lower calix). The approach described here involves retrieving the calculus, moving the retrieved calculus to a new (different) location which presents a larger space (e.g., the kidney or an upper calix) to perform lithotripsy or which presents a region where there is normal (non-damaged tissue) tissue.

Figure 4:
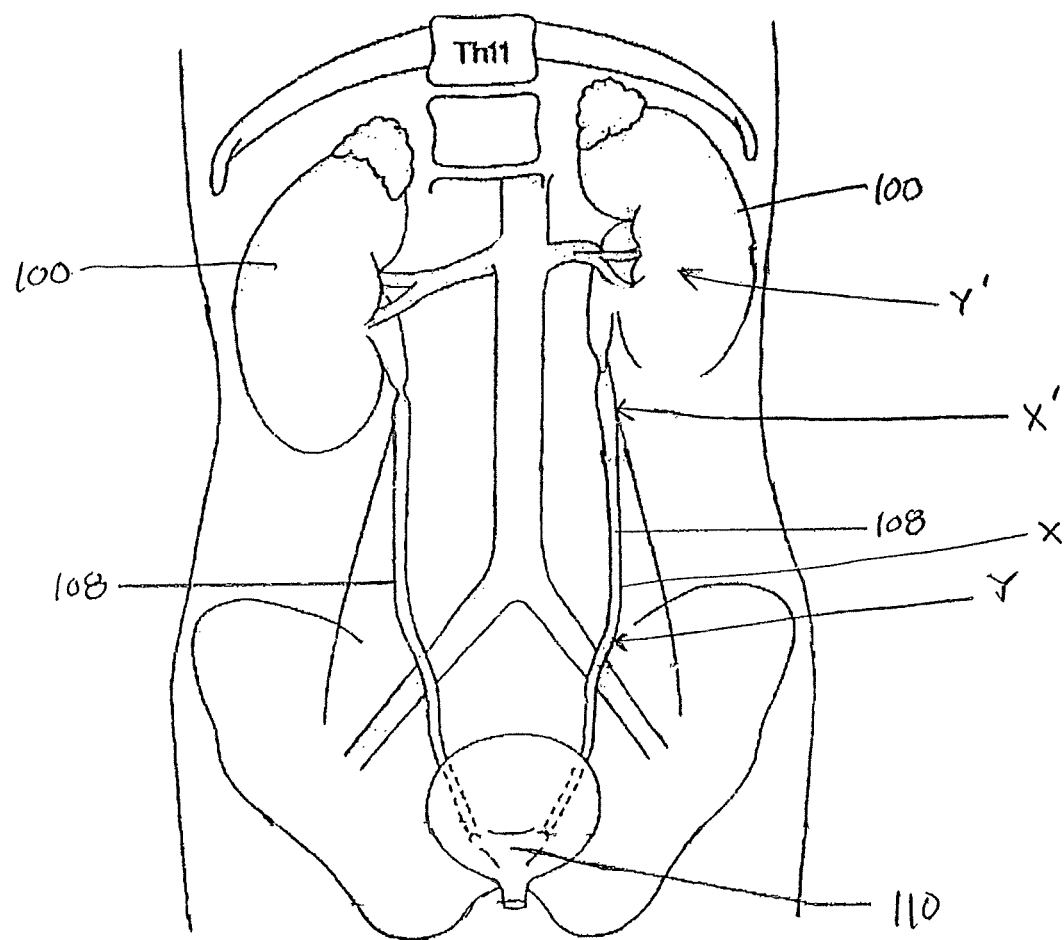
FIG. 4 is a schematic illustration of a portion of the human anatomy, including the urinary tract.

The retrieving device and system disclosed here can be used to retrieve calculus from a living body and remove the retrieved calculus from the living body. The retrieving device and system disclosed here are also configured to retrieve calculus from one place in the living body, move the retrieved calculus to a new (different) place in the living body where, for example, lithotripsy can be more easily performed to break-up the calculus, and then release the retrieved and moved calculus at the new location. By way of example, and with reference to FIG. 4, it is possible to retrieve calculus at the location X in the ureter (representing an example of a region of narrow size or damaged tissue) and move the retrieved calculus to the position X' in the ureter (representing an example of a region of larger size or normal non-damaged tissue). It is also possible to retrieve calculus at the location Y (representing an example of a region of narrow size or damaged tissue) and move the retrieved calculus to the position Y' in the kidney (representing another example of a region of larger size or normal non-damaged tissue). The retrieving device and system disclosed here are also well suited to retrieve calculus from a place in the living body, and removing the calculus from the living body.

Figure 6:
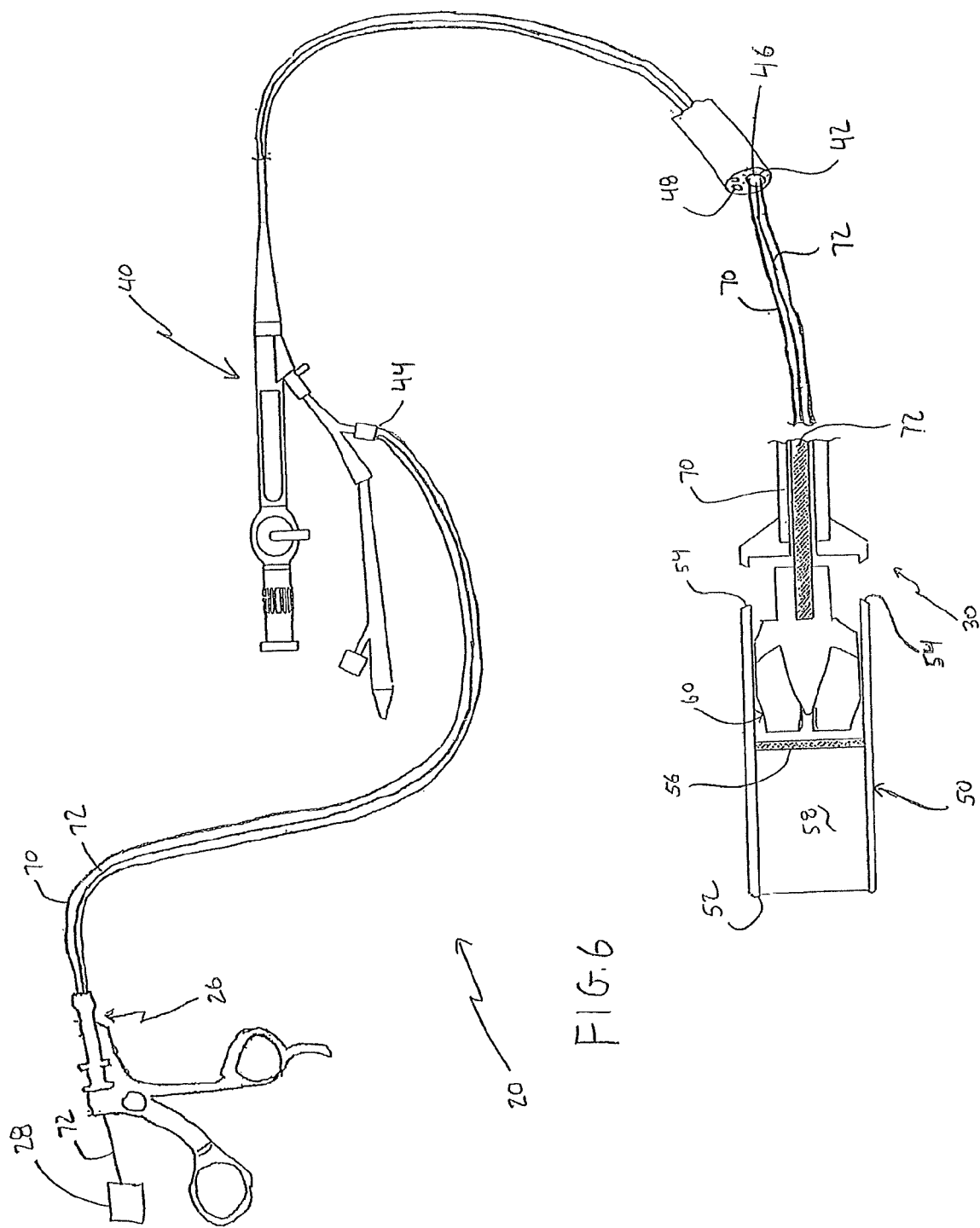
FIG. 6 is a schematic illustration of the retrieving system, including the retrieving device connected to the operation member through the intermediary of an elongated body such as an endoscope (ureteroscope).

To retrieve (and move) the calculus, a retrieving system such as the retrieving system 20 shown in FIG. 6 can be used. Specifically, the calculus retrieving device 30 is used, together with the operating member 26 and the endoscope (ureteroscope). The operating member 26 is connected to the shaft cover 70, so that operation of the operating member 26 causes the shaft cover 70 to move. That is, the operation of the operating member 26 causes the shaft cover 70 to axially move, which in turn causes the suction head 50 (including the impeller 60 and the filter 56) to also axially move. FIG. 6 schematically illustrates that the drive shaft 72 positioned within and extending along the axial length of the shaft cover 70 is connected to a driving device 28 (e.g., a geared motor). Operation of the driving device 28 rotates the drive shaft 72, which in turn rotates the impeller 60 positioned in the housing 51 of the suction head 50 of the calculus retrieving device 30. As shown in FIG. 6, the shaft cover 70 and the drive shaft 72 extend from the operating member 26, enter an inlet 44 of the instrument channel 42 in the ureteroscope 40, pass through the ureteroscope 40, and exit at an outlet at the distal end portion 46 of the ureteroscope 40.

In use, the shaft cover 70 is connected to the housing 51 of the suction head 50, and the proximal end of the shaft cover 70 and the drive shaft 72 are inserted into the outlet of the instrument channel 42 at the distal end portion 46 of the ureteroscope 40. The shaft cover 70 and the drive shaft 72 are pushed through the lumen (instrument channel 42) in the ureteroscope 40 until the proximal end of the shaft cover 70 and the proximal end of the drive shaft 72 exit out of the inlet 44 of the ureteroscope. The proximal end of the drive shaft 72 is then connected to the driving device 28, while the proximal end of the shaft cover 70 is fixed to the operating member 26.

In the case of the endoscope 40 being an ureteroscope, the ureteroscope is preferably a flexible ureteroscope. The ureteroscope 40 includes a viewing system that includes an objective lens or camera 48 schematically illustrated in FIG. 1 (and FIG. 16). In a known manner, this provides a field of view for the user or operator to facilitate carrying out the procedure involving locating calculus, retrieving the calculus, moving the calculus to the new location and releasing the calculus at the new location.

Figure 5:
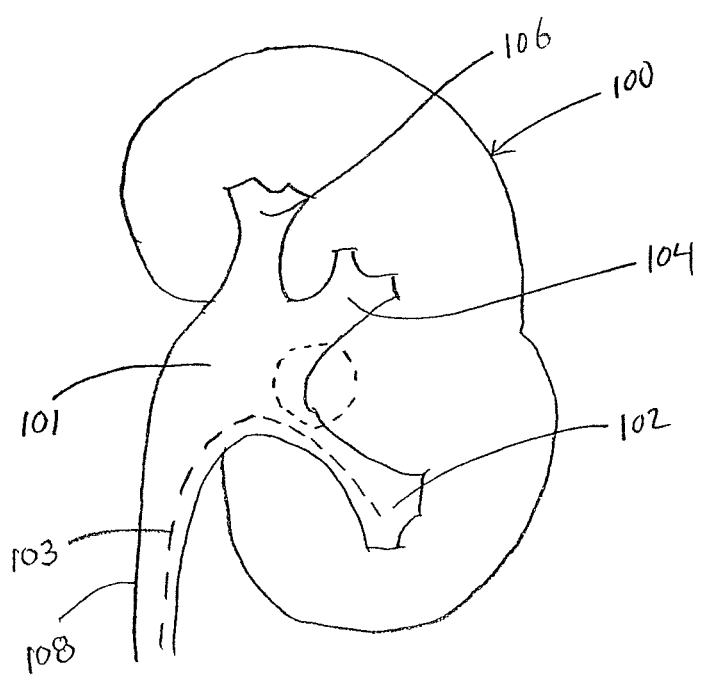
FIG. 5 is a schematic illustration of a human kidney, illustrating the renal pelvis, a lower calix (lower renal calix), a middle or intermediate calix (middle or intermediate renal calix), and an upper calix (upper renal calix).

FIG. 5 schematically illustrates a kidney and depicts various sections or regions of the kidney including the renal pelvis 101, a lower calix 102 (lower renal calix), a middle or intermediate calix 104 (middle or intermediate renal calix) and an upper calix 106 (upper renal calix). It is sometimes desirable to operate the access the lower calix 102 of the kidney to retrieve calculus located in the lower calix. To reach calculus in the lower calix 102 requires access by way of the ureter 108 along a path generally indicated by the dotted line 103 in FIG. 5. This path 103 can be rather difficult to navigate due to, for example, the highly curved configuration of the path which must be traversed to gain access to the lower calix 102, as well as the relatively narrow entrance to the lower calix 102. Another aspect of the disclosure here involves operational procedures or methods for facilitating access to the lower calix 102. It is to be understood that these methods or operational procedures are not limited to use in accessing the lower calix. Indeed, the methods can be used in a variety of other regions of the living body to help facilitate navigation to a target site in the living body. Also, the methods are not necessarily limited to retrieving calculus and are not limited to being performed solely with calculus retrieving devices. The operational procedures disclosed here can be implemented with other devices used together with an endoscope (ureteroscope) to access a desired target area or target site in the living body.

Part of the difficulty associated with navigating a highly curved portion of the living body and/or entering a rather narrow entrance region when using the device described above is that parts of the device are not well suited to traversing through a narrow region and/or along a highly curved path. For example, the suction head of the retrieval device has a rather significant length and is unable to bend. Similarly, the tip portion of the endoscope (ureteroscope) is incapable of being bent as it includes, for example, the camera or lens that allows visualization. Set forth below is a description of several operational procedures or methods which make it easier to traverse a narrowed region and/or a highly curved region.

It is known that endoscopes (ureteroscopes) are typically configured to allow the user or operator to bend/curve the distal end of the endoscope. Nevertheless, the extent of curving/bending, or the control of such curving/bending may be insufficient to access the lower calix, once again due to at least in part to the rather narrow entrance to the calix as well as the highly curved path required to reach the lower calix.

The methods or operational procedures described below help facilitate navigating a device through a highly curved area and/or into a narrow entrance region. The disclosed methods are described in the context of manipulating the retrieving device 30 described above to the lower calix. But the disclosed methods are not limited to navigating a calculus retrieving device and are not limited to navigating a device into the lower calix 102.

Figure 7A:
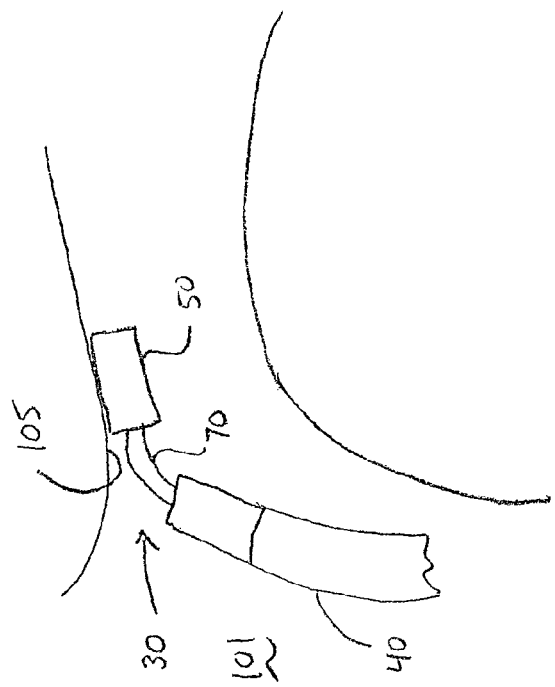
FIGS. 7A and 7B illustrate one embodiment of an operational procedure which can be carried out using the retrieving device illustrated in FIG. 1.
Figure 7B:
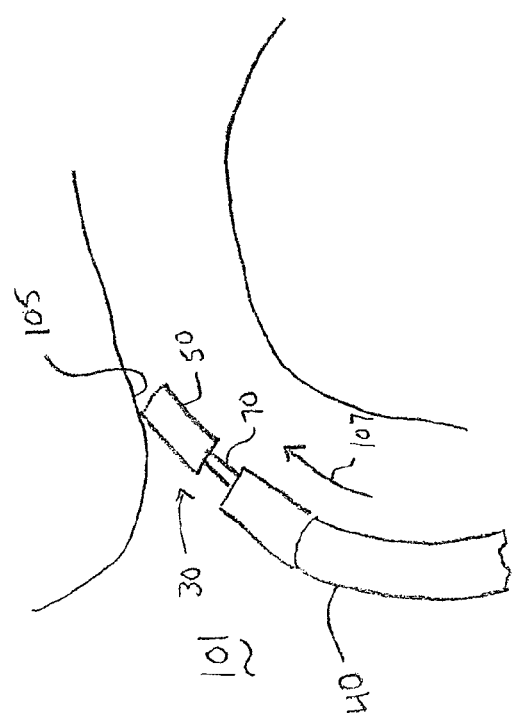

A first method is illustrated in FIGS. 7A and 7B. The method or operational procedure illustrated in FIGS. 7A and 7B depicts the endoscope 40, with the retrieving device 30, positioned in the renal pelvis 101. As is the case with the other methods described below, the endoscope 40 and the retrieving device 30 is positioned in the renal pelvis 101 by introducing the endoscope 40 (ureteroscope) together with the retrieving device 30 into the living body, advancing the endoscope 40 and the retrieving device 30 in the living body in the manner described above and ultimately introducing the endoscope 40 with the retrieving device 30 into the ureter 108 where the endoscope 40 and the retrieving device 30 are moved along the ureter 108. The illustration in FIG. 7A and 7B represents an enlarged view of the portion of the kidney circled in a dotted line in FIG. 5.

The method shown in FIGS. 7A and 7B involves moving the endoscope 40 (ureteroscope) and the retrieval device 30 in the axial forward direction after the endoscope 40 and the retrieval device 30 enter the renal pelvis 101. The retrieval device 30 is then moved axially forward relative to the endoscope 40 (e.g., forward movement of the retrieval device 30 is stopped while forward movement of the retrieval device 30 continues). This causes a portion of the cover shaft 70 to be exposed outside the instrument channel of the endoscope 40 so that a portion of the cover shaft 70 extends distally beyond the distal end of the endoscope 40. Continued axial forward movement of the retrieval device 30 relative to the endoscope 40 and/or forward movement of the endoscope 40 with the retrieval device 30 causes the distal end of the retrieval device 30 (the distal end of the suction head 50) to contact a wall 105 of the kidney (living body) as shown in FIG. 7A. To help ensure that the distal end of the suction head 50 is moved towards and into contact with the wall 105 of the kidney, the endoscope's viewing/imaging system (i.e., the objective lens or camera 48) can be used. That is, the operator can use the endoscope's viewing/imaging system 48 to view the forward movement of the retrieval device 30 (suction head 50) and guide the suction head 50 into contact with the wall 105 of the living body.

After the distal end of the suction head 50 is brought into contact with the wall 105 of the living body, the endoscope 40 (with the suction head 50) continues to be pushed or moved axially forward toward the direction that is the same as the direction of insertion required to approach the target area or target site (e.g., the lower calix). That is, after the suction head 50 contacts the wall of the living body, the endoscope 40 together with the suction head 50 (the endoscope 40 and the suction head 50 move together as a unit) continues to be moved in the direction of insertion (indicated by the arrow 107 in FIG. 7A) to approach the target area. This causes the shape of the retrieving device 30 to change from the shape shown in FIG. 7A to a shape like that shown in FIG. 7B. More specifically, the shaft cover 70 bends as generally illustrated in FIG. 7B to change the angular orientation of the suction head 50 relative to the endoscope 40. During this operational procedure, only the exposed portion of the shaft cover 70 is bent. This is attributable to several factors. The distal end portion of the endoscope 40 and the suction head 50 are made from a solid material (relatively rigid material) and so a relatively large force is required to bend the endoscope 40 and the suction head 50. On the other hand, the shaft cover 70 is made from a relatively soft material (e.g. an elastic tube) and so when an external force is applied around the tip portion of the retrieving device 30 (i.e., the distal end portion of the endoscope 40, the suction head 50 and the exposed part of the shaft cover 70), the exposed shaft cover 70 tends to be more easily bent. Also, once the exposed shaft cover 70 bends a little, the force applied by the pushing of the endoscope 40 (with the retrieval device 30) tends to concentrate on the bent portion of the exposed shaft cover 70. In this situation, the contact area between the suction head 50 and the wall 105 of the living body works as the fulcrum point, and the operator's hand pushing the endoscope 40 works as the point of effort, and the exposed shaft cover 70 works as the point of load. The description which follows refers to the shaft cover 70 being bent or curved. It is to be understood that the bending or curving of the shaft cover 70 means that the drive shaft 72 located inside the bent or curved portion of the shaft cover 70 is similarly bent or curved.

In the position shown in FIG. 7A, the central axis of the suction head 50 is oriented at a first angular orientation relative to the central axis of the distal end portion of the endoscope 40 (ureteroscope). Later, after the endoscope 40 and the suction head 50 move together following the contact of the suction head 50 with, the central axis of the suction head 50 is oriented at a second angular orientation relative to the central axis of the distal end portion of the endoscope 40 (the second angular orientation differs from the first angular orientation). After this bending, the endoscope 40 is moved in the direction of insertion 107 toward the target site (i.e., the lower calix), with the suction head 50 ultimately being positioned in at the target site target site or lower calix to retrieve calculus in the lower calix. With the shaft cover 70 bent or curved in the manner illustrated in FIG. 7B, it is easier to navigate the extreme curvature leading toward the target site (i.e., the lower calix) as well as the narrow entrance leading to the target site.

It is possible to vary the degree of bending of the shaft cover 70 by varying the length of the shaft cover 70 that is exposed outside the instrument channel of the endoscope 40. For example, the endoscope 40 and the suction head 50 which have entered the renal pelvis 101 can be stopped at a first position spaced a first distance from the wall 105 of the living body. Then, the suction head 50 is moved axially forward relative to the endoscope 40 so that the distal end of the suction head 50 contacts the wall 105 of the living body. At this time, a first length of the cover shaft 70 is exposed outside the instrument channel of the endoscope 40. When the endoscope 40 and the suction head 50 are both moved forward at this time, the shaft cover 70 will bend or curve a first amount. On the other hand, the endoscope 40 and the suction head 50 which have entered the renal pelvis 101 can be stopped at a second position spaced a second distance from the wall 105 of the living body, where the second distance is greater than the first distance. Then, the suction head 50 is moved axially forward relative to the endoscope 40 so that the distal end of the suction head 50 contacts the wall 105 of the living body. At this time, a second length of the cover shaft 70 is exposed outside the instrument channel of the endoscope 40, where the second length is greater than the first length. When the endoscope 40 and the suction head 50 are both moved forward at this time, the shaft cover 70 will bend or curve a second amount which is greater than the first amount.

Figure 8C:
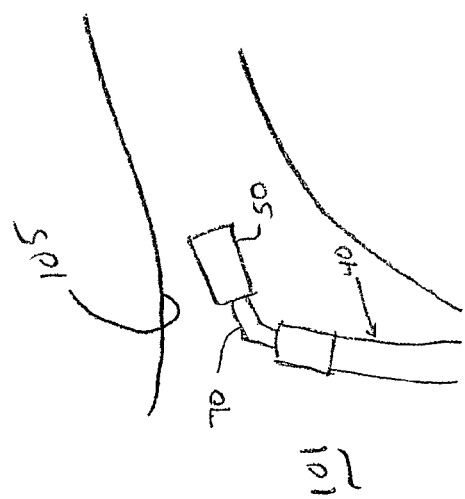
FIGS. 8A-8C illustrate another embodiment of an operational procedure which can be carried out using the retrieving device illustrated in FIG. 1.
Figure 8B:
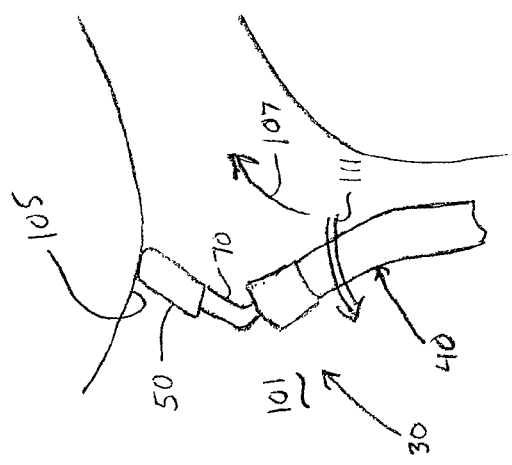
Figure 8A:
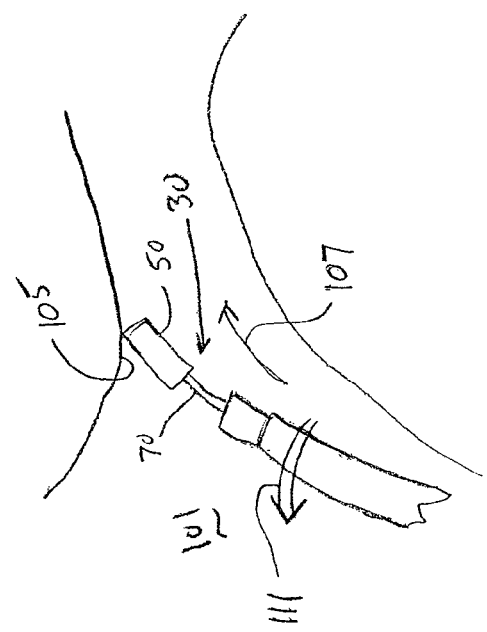

FIGS. 8A-8C illustrates another method or operational procedure that is slightly different from the procedure shown in FIGS. 7A and 7B. This procedure shown in FIGS. 8A-8C is the same as the procedure described above with respect to the embodiment shown in FIGS. 7A and 7B, except in one respect. After the retrieval device 30 (suction head 50) is brought into contact with the wall 105 of the living body as illustrated in FIG. 8A, the endoscope 40 is deflected in a direction different from the direction of insertion to approach the target area. FIG. 8B illustrates the direction of insertion to approach the target area (i.e., lower calix in this example) by way of the single-line arrow 107 in FIGS. 8A and 8B, whereas the direction of deflection of the endoscope 40 is indicated by the double-line arrow 111 directed towards the left in FIGS. 8A and 8B. As is known in the art, endoscopes are typically configured so that through operation or manipulation of a hand operation part of the endoscope 40, the distal portion of the endoscope 40 can be deflected (bent or curved). The direction of deflection of the endoscope 40 indicated by the double-line arrow in FIGS. 8A and 8B refers to manipulation or operation by the operator that causes the distal end of the endoscope 40 to be deflected as illustrated.

Thus, in the embodiment described above and shown in FIGS. 7A and 7B, the cover shaft 70 is bent (the shape of the retrieval device 30 is changed) by moving the endoscope 40 and the suction head 50 in the direction of insertion to approach the target area (i.e., in the direction 107 in FIG. 7A), whereas in the embodiment described above and shown in FIGS. 8A-8C, the cover shaft 70 is bent (the shape of the retrieval device 30 is changed) by deflecting the distal portion of the endoscope 40 in a direction 111 different from, and away from (opposite to), the direction of insertion to approach the target area (direction 107). The embodiment of the procedure shown in FIGS. 8A-8C is quite effective in bending the shaft cover 70.

In this procedure shown in FIGS. 8A-8C in which the direction of deflection 111 of the endoscope 40 differs from or is opposite to the direction 107 of insertion to approach the lower calix, it is necessary after the shaft cover 70 is bent or curved to change the angular orientation of the suction head, to take back the deflected endoscope 40, to deflect the endoscope 40 in the opposite direction from the direction 111 or otherwise operate the endoscope to angle the endoscope 40 in the direction toward the target direction 107. This is illustrated in FIG. 8C. From the position shown in FIG. 8B, the endoscope 40 is deflected in the opposite direction from the direction 111 (i.e., toward the direction 107 of insertion) to cause the endoscope 40 to be reoriented in the manner illustrated in FIG. 8C. After this re-deflection, the endoscope 40 is moved in the direction 107 of insertion to approach the target site (i.e., the lower calix) to then advance the endoscope and the suction head and position the suction head within the target site or lower calix. The shaft cover 70 bent or curved in the manner illustrated in FIG. 8C is better able to traverse the sharply curvature leading toward the target site (i.e., the lower calix) as well as the narrow entrance to the target site.

Figure 9C:
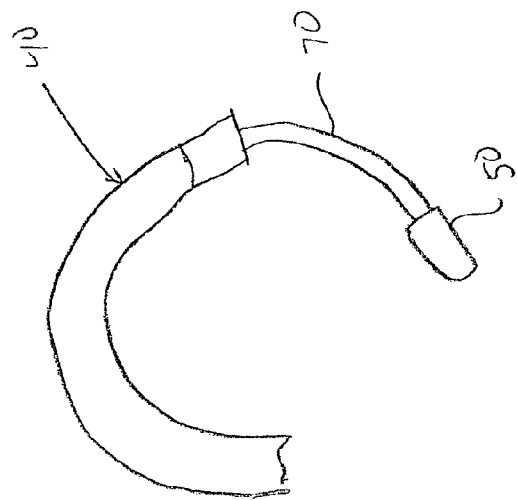
FIGS. 9A-9C depict another embodiment of an operational procedure which can be carried out using the retrieving device illustrated in FIG. 1.
Figure 9B:
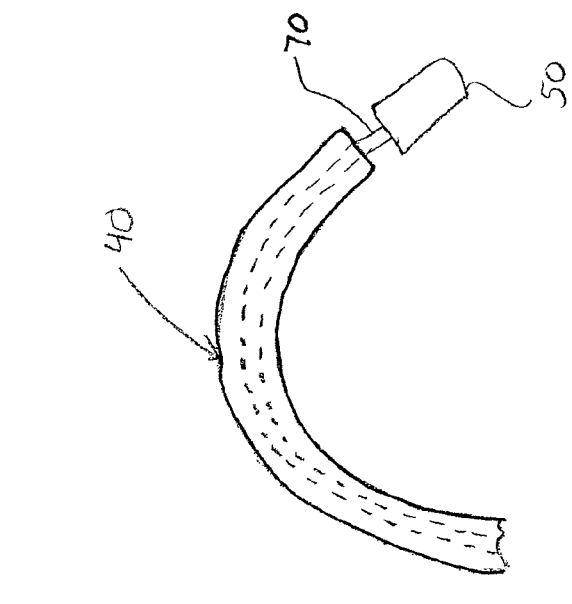
Figure 9A:
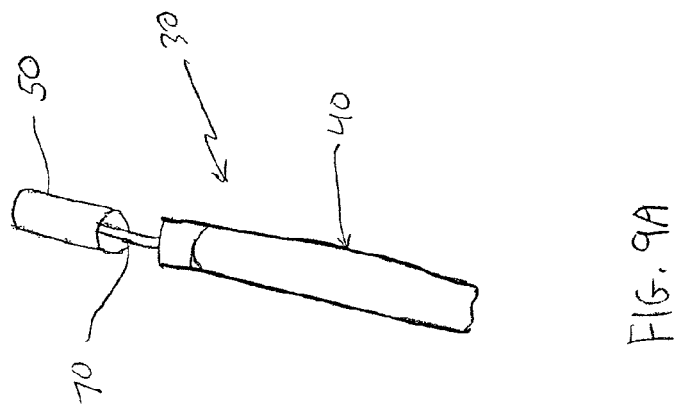

FIGS. 9A-9C illustrate another method of altering the shape of the retrieval device 30 by curving or bending the shaft cover so that the retrieval device 30 can be more easily moved through the sharp curvature and narrow entrance leading to the target site. FIG. 9A illustrates the retrieval device 30 prior to introduction into the living body. The endoscope 40 and retrieval device 30 are introduced into the living body such as in the manner described above, and are eventually introduced into and moved along the ureter 108 as also described above so that the endoscope 40 and the retrieval device 30 eventually enter the renal pelvis 101.

In a manner known in the art, the endoscope 40 (ureteroscope) is configured so that through operation or manipulation of the hand operation part of the endoscope 40, the distal end of the endoscope 40 bends or curves along its length. This bending of the distal portion or distal region of the endoscope 40 can be performed the endoscope 40 is located in and moving the living body. When the distal end portion of the endoscope 40 and the retrieval device 30 enter the renal pelvis, the hand operation part of the endoscope 40 is operated or manipulated to cause the distal end region of the endoscope 40 to bend or curve (change its shape) such as in the manner illustrated in FIG. 9B. This bending or curving of the distal end region of the endoscope 40 also causes the distal portion of the shaft cover 70 (which is located in the instrument channel of the endoscope 40) to curve or bend (change its shape) in a manner similar to the bent distal end region of the endoscope as also shown in FIG. 9B. Retaining or maintaining this bent or curved state of the distal end region of the endoscope 40 and the shaft cover 70 to some extent causes a non-invertible (non-reversible) shape change of the shaft cover 70. The shape of the shaft cover 70 is thus changed from straight to curving. In this embodiment, the shaft cover 70 is fabricated in such a manner that, when bent, curved or altered in shape, the shaft cover 70 maintains the bent, curved or changed shape. These characteristics of the shaft cover 70 can be achieved by suitably selecting the thickness and/or the orientation of the polymer molecule of tubes. Materials which can be used to fabricate the shaft cover 70 include polyethylene, polyurethane, nylon elastomer, polyester elastomer, polystyrene elastomer, polyimide, polycarbonate, fluoropolymer, porous fluoropolymer, polyolefin, silicone rubber, chloroethene, polyvinyl chloride, etc. The shaft cover 70 can also be configured as a coil or spring. By virtue of the change in shape of the distal end of the endoscope 40 (instrument channel in the endoscope) the shaft cover 70 takes on a certain set or certain curvature that is generally determined by the curvature of the instrument channel in the endoscope 40. According to this embodiment of the method or operational procedure, the operator deflects the distal end region of the endoscope 40, preferably in the renal pelvis or commodious area of the kidney, to bend the shaft cover 70 before inserting the endoscope 40 with the suction head 50 toward the curved lumen (e.g., the curved lumen leading toward the lower calix). The shaft cover 70 is in the form of a tube or a tubular member.

After the distal end region of the endoscope 40 is curved, bent of otherwise changed in shape, the shaft cover 70 is moved in the forward or distal direction relative to the endoscope 40 as illustrated in FIG. 9C. The shaft cover 70 is thus exposed outside the instrument channel in the endoscope 40, but nevertheless maintains the curved or bent configuration that is imparted to the shaft cover 70 by bending or curving the distal end region of the endoscope 40 (i.e., the instrument channel in the endoscope). FIG. 9C depicts the distal end of the shaft cover 70 exposed outside the instrument channel and maintaining the previously set curved or bent configuration. This allows the suction head 50 to traverse a highly curved region and also allows the suction head 50 to enter a rather narrow region such as that necessary to position the suction head 50 in the lower calix.

In each of the operational procedures described above, the change in shape or orientation of the retrieval device 30 occurs while the endoscope 40 (with the suction head 50 and the shaft cover 70) are positioned in the living body. It is also possible to impart curvature to the retrieval device 30 before the endoscope 40 (with the suction head 50 and the shaft cover 70) are introduced into the living body. An example of this is illustrated in FIG. 10.

Figure 10:
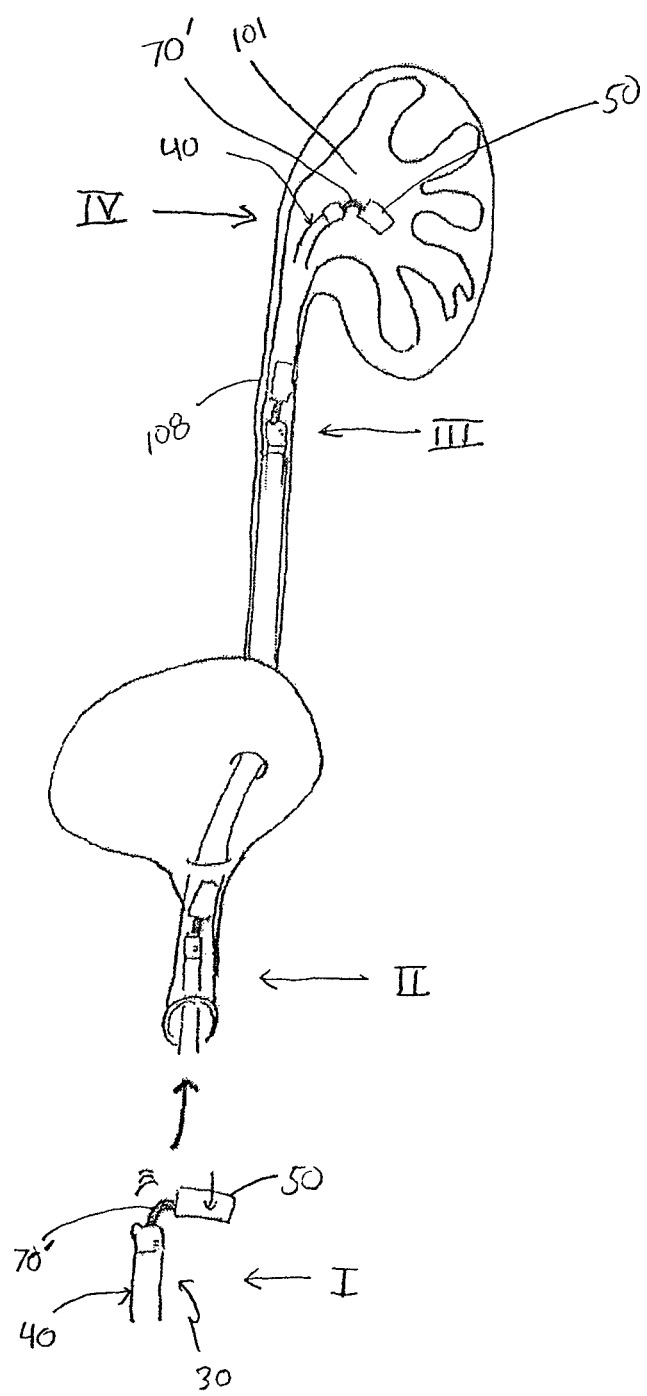
FIG. 10 shows a further embodiment of an operational procedure which can be carried out using the retrieving device illustrated in FIG. 1.

FIG. 10 illustrates four different aspects of this operational procedure. The four aspects are identified as I, II, III and IV. This embodiment of the operational procedure shown in FIG. 10 begins at I where, prior to introducing the retrieval device 30 into the living body, the distal portion of the shaft cover 70' is bent or curved so that the central axis of the suction head 50 is oriented at a first angular orientation (other than 180°) relative to the central axis of the distal end portion of the endoscope 40. In this embodiment, the shaft cover 70' is made of a material which imparts shape-memory characteristics to the shaft cover (tube or tubular member). Shape-memory characteristics can be realized by suitably selecting the thickness and/or the orientation of the polymer molecule of tubes. Materials which can be used to fabricate the shaft cover 70' include polyethylene, polyurethane, nylon elastomer, polyester elastomer, polystyrene elastomer, polyimide, polycarbonate, fluoropolymer, porous fluoropolymer, polyolefin, silicone rubber, chloroethene, polyvinyl chloride, etc. The preferable material is a kneading polypropylene tube. It may also be possible to heat a bent tube to impart shape-memory characteristics to the bent tube and thus form a shaft cover 70' exhibiting shape-memory.

Next, as indicated at II, the curved shaft 70' possessing the curved or bent shape is somewhat straightened, and then the endoscope 40 along with the shaft cover 70' and the suction head 50 are introduced into the living body or a lumen in the living body as previously described above. The straightening of the curved or bent shaft cover 70' to change the angular orientation of the central axis of the suction head 50 relative to the central axis of the distal portion of the endoscope 40 is preferably accomplished manually by the user or operator as a part of introducing the endoscope 40 along with the shaft cover 70' and the suction head 50 into the lumen of the living body. The straightening experienced by the shaft cover 70' need not fully straighten the shaft cover 70'. Indeed, the shaft cover 70' is straightened to the extent required to position the endoscope 40 (and the shaft cover 70' and the suction head 50) in the living body lumen and moved along the living body lumen. The endoscope 40, together with the suction head 50 and the shaft cover 70', are then moved axially forward (axially advanced) within the living body. Because the lumen in the living body into which the endoscope 40 and the suction head 50 and shaft cover 70' are introduced is rather small in size and not much larger in inner diameter than the outer diameter of the endoscope 40 (and suction head 50), the living body lumen applies a force to the somewhat straightened shaft cover 70' that maintains the shaft cover 70' in the straightened shape while the endoscope 40 (and suction head 50 and shaft cover 70') are located in the living body lumen.

As illustrated at III at FIG. 10, with continued forward axial movement of the endoscope 40 (and suction head 50 and shaft cover 70'), the distal end portion of the endoscope 40, and the suction head 50 and the shaft cover 70', enter the ureter 108 and are axially moved along the ureter 108. Once again, the size of the ureter 108 is rather small and not much larger in inner diameter than the outer diameter of the endoscope 40 (and suction head 50), and so the ureter 108 applies a force to the somewhat straightened shaft cover 70' that maintains the shaft cover 70' in the straightened shape while the endoscope 40 (and suction head 50 and shaft cover 70') are located in the ureter.

Continued forward movement of the endoscope 40 (and suction head 50 and shaft cover 70') causes the distal end portion of the endoscope 40 together with the suction head 50 and the shaft cover 70' to enter the renal pelvis 101 as shown at IV in FIG. 10. The size of the renal pelvis 101 is larger than the size (inner diameter) of the ureter 108 and so, by virtue of the suction head 50 and the shaft cover 70' entering the enlarged space in the renal pelvis 101, the shaft cover 70' is no longer maintained in the somewhat straightened shape by the wall of the ureter 108. The shaft cover 70' is thus free to take on or return toward its curved or bent shape, namely the shape it had before being introduced into the living body (i.e., the configuration at step I prior to introducing the endoscope 40, with the suction head 50 and shaft cover 70', into the living body lumen). The curved shaft cover 70' need not fully return to the same exact curved or bent shape that the shaft cover 70' possessed before introduction into the living body. Rather, it is sufficient that the shaft cover 70', upon entering the renal pelvis 101, changes from the somewhat straightened shape exhibited by the shaft cover 70' when located in the ureter 108 toward the curved or bent shape exhibited by the shaft cover 70' before introducing the endoscope 40, with the suction head 50 and shaft cover 70', into the living body lumen. The curved or bent shape of the retrieving device 30 (shaft cover 70') allows the suction head 50 to be introduced into the rather narrow passage leading to the lower calix, and also allows the suction head 50 to traverse tight curvature needed to navigate towards the lower calix.

In this embodiment, the shaft cover 70' is made of a material which allows the shaft cover 70' to be bent and to maintain the curved or bent shape. The material forming the shaft cover 70' is also selected so that when the shaft cover is straightened through the application of an external force or load, like that encountered when the shaft cover possessing the bent or curved shape is positioned in the living body lumen, the shaft cover will return toward its curved or bent shaped when entering the enlarged space of the renal pelvis (i.e., when the force or load is removed or no longer applied.

Depending upon a variety of factors including the bent or curved configuration of the shaft cover 70', the material forming the shaft cover 70, and the particular configuration of the kidney (lower calix), the curved or bent shaft cover 70' may not be sufficiently return to its bent or curved shape when entering the renal pelvis (i.e., when reaching the position illustrated at IV in FIG. 10). In that situation, the operational procedure described above and illustrated in FIGS. 7A-9C can be utilized to further bend or curve the cover shaft 70' and orient the suction head 50 in a way facilitating entry into the narrow and highly curved passage leading to the lower calix.

Figure 11A:
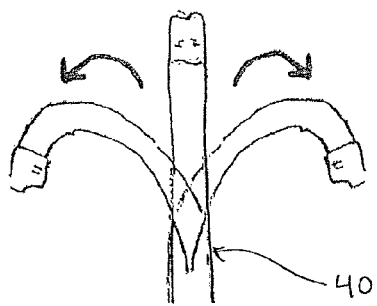
FIGS. 11A-11C are schematic illustrations of the distal end of the endoscope showing several different ways in which the distal end of the endoscope can deflect during use and a manner of addressing deflections in an undesirable direction.
Figure 11B:
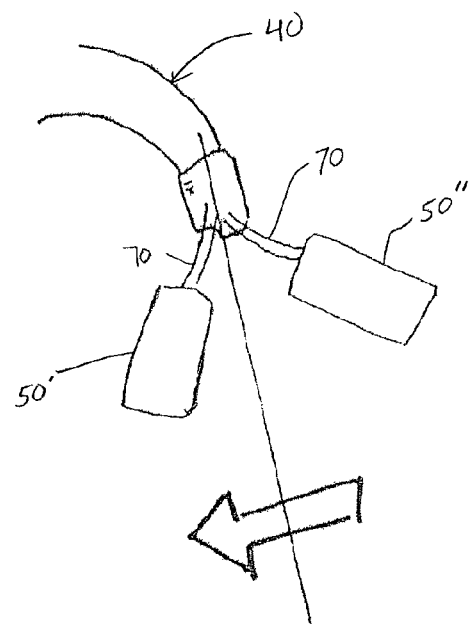

While the operational procedures described above and illustrated in FIGS. 7A-10 are carried out, the distal end portion of the endoscope 40 may tend to deflect on its own. Depending upon the procedure, the deflection may be a preferable deflection or may be deflection in a direction that is not desirable. FIG. 11A illustrates the distal end portion of the endoscope being deflected both to the left and the right from a central or straight position. FIG. 11B illustrates the distal end portion of the endoscope 40 (ureteroscope) and illustrates an undesirable relationship between the direction of deflection of the distal end portion of the endoscope 40 (ureteroscope) and the direction of deflection of the suction head (shaft cover 70 to the right. By virtue of this deflection of the distal end of the endoscope 40 in the undesired direction, the suction head 50" is directed along an undesirable movement path. FIG. 11B also depicts a preferable direction of bending of the distal end of the endoscope 40 indicated by the position of the suction head 50'.

Figure 11C:
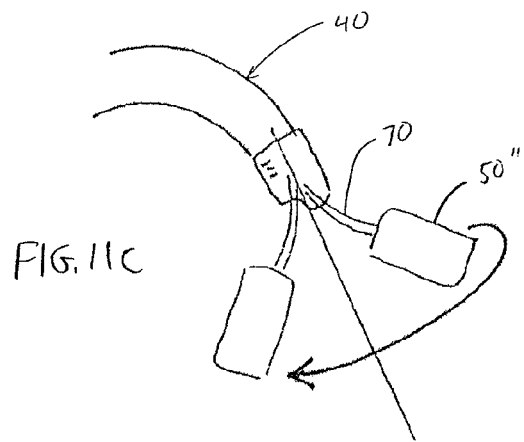

FIG. 11C illustrates that the undesirable or non-preferable direction of bending of the distal end of the endoscope 40 (and the suction head 50") can be converted to bending of the distal end of the endoscope 40 in the preferable direction by simply rotating the shaft cover 70 (suction head 50") distal end portion of the endoscope 40 (ureteroscope) as noted by the arrow in FIG. 11C, thus causing the suction head 50" to be shifted for movement along a desired path of movement.

The embodiments of the retrieving system and operational procedure described above and illustrated in FIGS. 7A, 7B, 8A-8C and 9 involve a shaft cover 70' made of material that can be re-shaped (re-shapable material). On the other hand, the embodiment described above and shown in FIG. 10 includes a shaft cover 70' made of material that retains its shape (shape-memory material) that is able to retain its bent or curved shape when an applied force is later removed. In the embodiments described above, the shaft cover 70 and 70' are in the form of a tube or tubular member. The tubular shaft cover 70 and 70' can take one of several forms to exhibit the re-shapeable and/or shape-memory characteristics described above.

Figure 12:
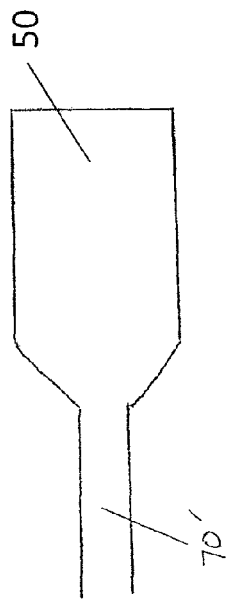
FIG. 12 illustrates the suction head connected to the distal end of the shaft cover, wherein the shaft cover is made of a material allowing the shaft cover to exhibit desired characteristics.

FIG. 12 illustrates one such possibility in which the shaft cover 70' is made of a tube of engineering plastic material. Examples of such material include polyethylene, polyurethane, nylon elastomer, polyester elastomer, polystyrene elastomer, polyimide, polycarbonate, fluoropolymer, porous fluoropolymer, polyolefin, silicone rubber, chloroethene, polyvinyl chloride, etc.

Figure 13:
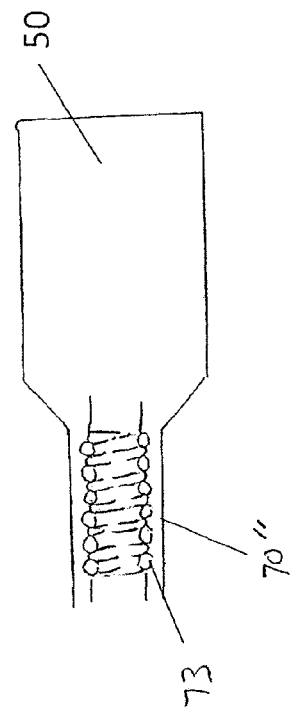
FIG. 13 illustrates the suction head connected to the distal end of the shaft cover, wherein the shaft cover possesses a different construction allowing the shaft cover to exhibit desired characteristics.

FIG. 13 illustrates another possible configuration for the shaft cover. Here, the shaft cover 70" is in the form of a tube made of engineering plastic material similar to that described above with respect to FIGS. 7A-10, but in addition a stainless steel coil 73 is fused inside the tube of engineering plastic material forming the shaft cover 70". Thus, in this embodiment shown in FIG. 13, the shaft cover is comprised of the combination of the coil 73 and the tube 70" made of plastic material. The coil advantageously imparts kink resistance characteristics to the lumen of the shaft cover 70" so that the shaft inside the shaft cover 70" (i.e., the drive shaft 72) is not hindered in its rotation. In addition, the stainless steel coil 73 fused to engineering plastic material can bring out the shape-memory feature because the engineering plastic material existing in a clearance gap of the stainless steel coil can weaken a restoring force of the stainless steel coil, and the stainless steel coil 73 fused to the lumen of the engineering plastic material tube can increase a bendability (kink resistance) of the engineering plastic material tube. An adjustment of the balance between the restoring force of the stainless steel coil and bendability of the engineering plastic material tube can generate a desirable shape-memory feature.

Figure 14:
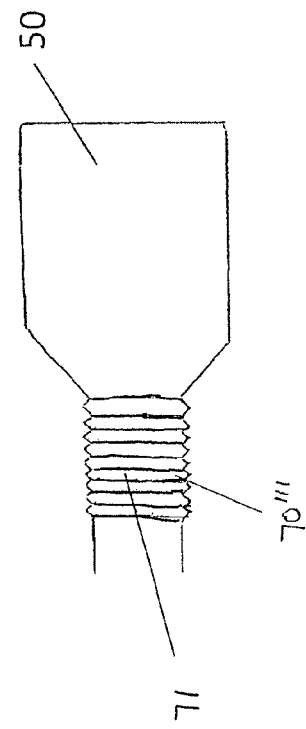
FIG. 14 illustrates the suction head connected to the distal end of the shaft cover, wherein the shaft cover possesses another construction allowing the shaft cover to exhibit desired characteristics.

A third possibility for the shaft cover is illustrated in FIG. 14. The shaft cover 70'" in this embodiment is in the form of a tube possessing an accordion-shaped portion 71. This configuration of the shaft cover 70'" is similar to the configuration of bendable straws that can be bent to a bent shape and retained in the bent shape. This embodiment of the shaft cover 70'" may be better suited for use with the embodiment shown in FIGS. 7A-8C.

An example of a shape-memory tube for the shaft cover 70 is a kneading polypropylene tube, and examples of re-shapeable tubes for the shaft cover 70' are kneading polypropylene and polyurethane.

A still further embodiment of the disclosure here is illustrated in FIGS. 15A-15D. These figures illustrate an embodiment of the suction head 150 in which the suction head 150 is connected to a hinge bracket 160 by way of a hinge pin 152. The hinge bracket 160 includes a lumen or hole 162 and a lumen or hole 164. The hole size of the lumen or hole 162 is larger than the size of the lumen or hole 164. The lumen or hole 162 is configured to receive the distal end portion of the cover shaft 70 and the lumen/hole 162 and the lumen/hole 164 are configured to be inserted by the distal end portion of the drive shaft 72. It is to be understood that the suction head 150 internally houses features like those housed inside the suction head 50 as shown in FIGS. 1 and 2 such as the filter, the impeller, etc. Those features are not specifically illustrated in FIGS. 15A-15D for convenience of illustration.

Figure 15A:
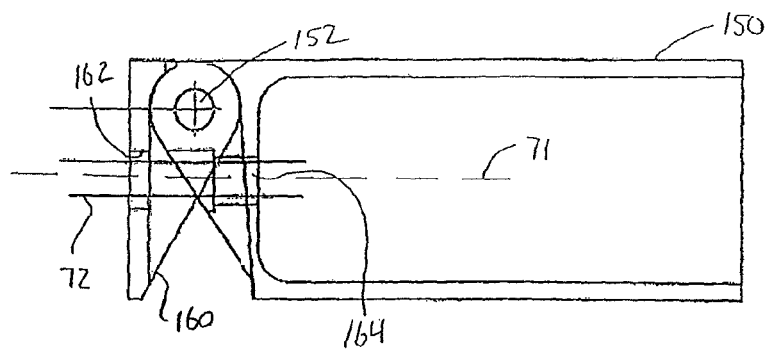
FIGS. 15A-15D illustrate an embodiment of a suction head that allows the angle between the suction head and the shaft cover to be varied.
Figure 15B:
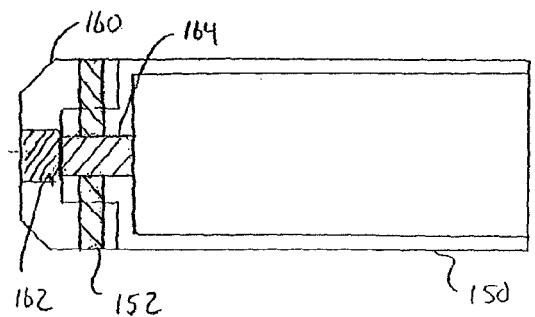

The hinged configuration of the suction head 150 illustrated in FIGS. 15A and 15B allow the angular orientation of the central axis 151 of the suction head 150 to be changed relative to the central axis 71 of the distal end portion of the shaft cover 70. The suction head 150 rotates about the hinge pin 152. The drive shaft 72 is less angled compared to the suction head 150 because the relatively larger lumen/hole 162 can reduce the degree of kink of the drive shaft 72. The angle of the drive shaft 72 is decreased by the clearance between lumen 162 and the drive shaft 72. This clearance can be realized or generated because the size of the hole 162 is larger than the size of the hole 164.

The hinged connection of the suction head shown in FIGS. 15A and 15B can be used to carry out the operational procedure illustrated in FIGS. 7A-7C. That is, the hinged suction head 150 can be moved into contact with the wall of the body tissue to cause the suction head 150 to change its angular orientation relative to the shaft cover 70 so that the central axis 151 of the suction head 150 relative to the central axis 71 of the distal end portion of the shaft cover 70 changes from a first angular orientation to a second angular orientation.

Figure 15C:
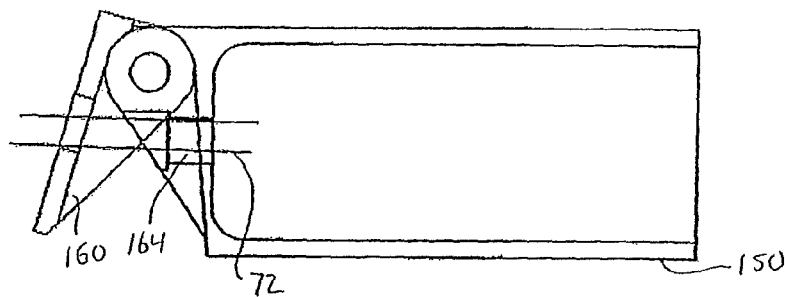
Figure 15D:
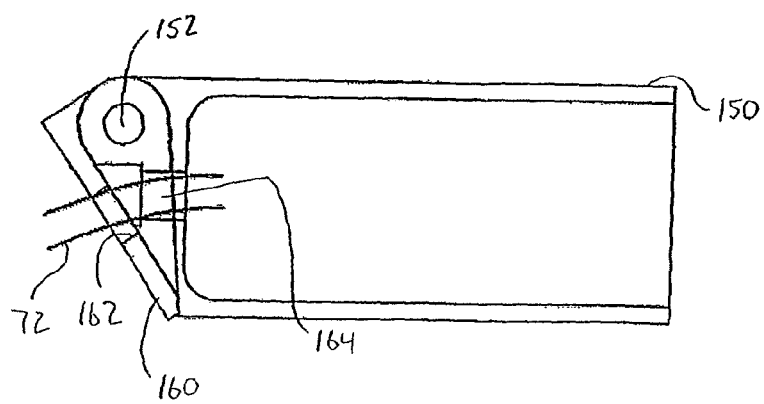

FIG. 15C illustrate the suction head 150 being angled at a 10° angle in one direction (up). Thus, the central axis of the suction head 150 forms an angle of 10° relative to the central axis of the distal end portion of the shaft cover 70. FIG. 15D illustrates an alternative position of the suction head 150 in which the suction head 150 is angled at a 35° angle in the opposite direction (down) relative to the distal end portion of the shaft cover 70. Thus, the central axis of the suction head 150 forms an angle of 35° relative to the central axis of the distal end portion of the shaft cover 70. The suction head 150 can be retained at any angular position between the state shown in FIG. 15C and the state shown in FIG. 15D. The suction head 150 can thus be operated like the re-shapeable shaft cover 70 shown in FIGS. 7-8. A suitable retaining force for retaining the suction head at the desired angular orientation can be achieved by, for example, adjusting the clearance of the hinge pin 152. That is, a relatively tight fit between the hinge pin 152 and the hole in which the hinge pin 152 fits can create a position retaining force that retains the suction head 150 at the desired angular orientation. In addition, in the state shown in FIGS. 15C and 15D, the drive shaft 72 is less angled compared to the suction head 150 because the larger lumen/hole 162 can reduce the degree of kink of the shaft. The drive shaft 72 is thus able to rotate relatively smoothly in any position between the angled states shown in FIGS. 15C and 15D. Pivoting the suction head 150 about the hinge pin 152 makes it possible to change the shape of the retrieving device 30 in a way allowing the suction head 150 to be introduced into the rather narrow passage leading to the lower calix and to be severely curved to navigate towards the lower calix. The range of angular adjustment permitted by the hinge bracket 160 depends on the size of the hinge bracket. Increasing the range of angular adjustment typically requires a larger (longer) hinge bracket 160. In this example, the length of the hinge bracket 160 is 2 mm to avoid increasing the total length of the suction head. This length of hinge bracket 160 provides a permissible angular range of adjustment of between −35 degrees and 10 degrees.

Figure 16:
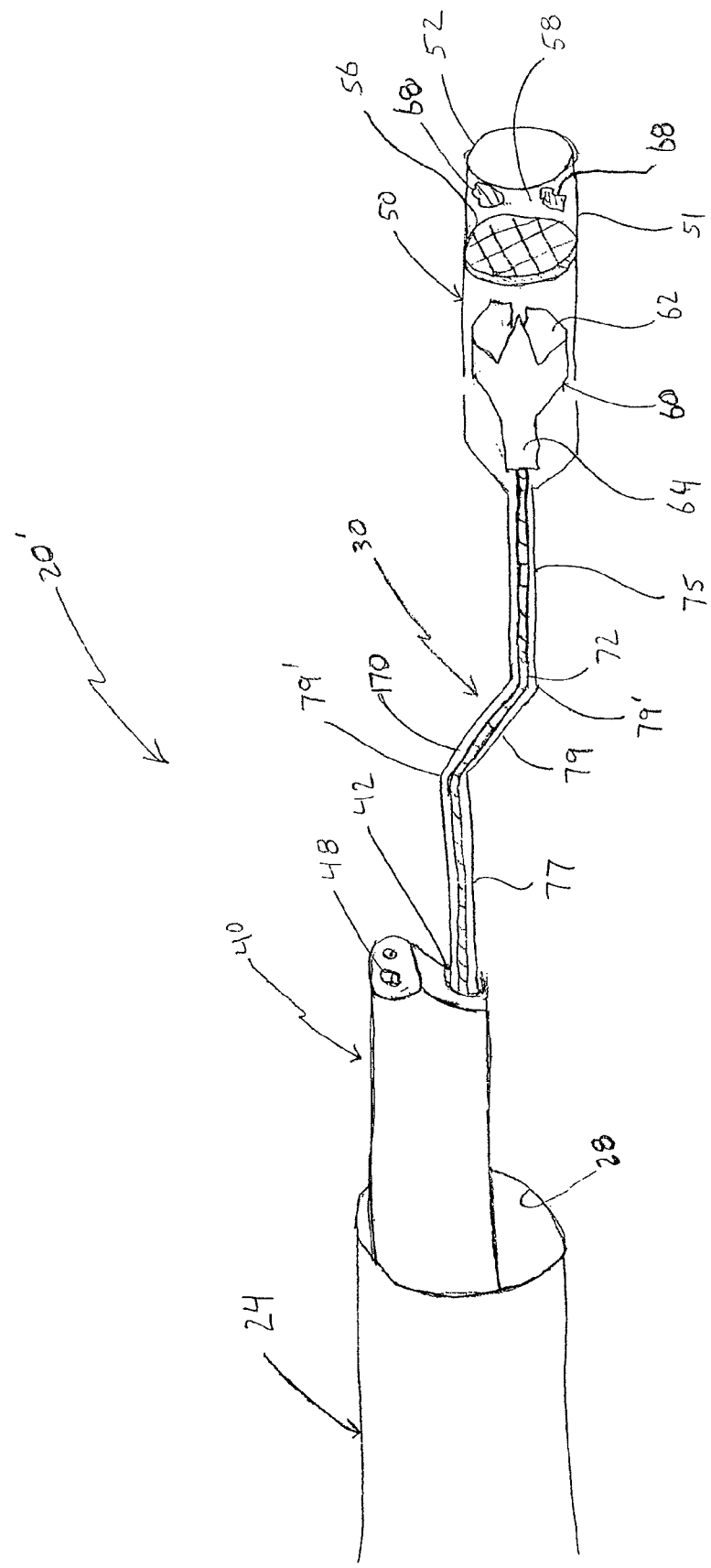
FIG. 16 is a schematic illustration similar to FIG. 1, but illustrating a modified system utilizing a cover shaft possessing a different configuration.

FIG. 16 is a schematic illustration of another system for retrieving calculus/calculi from a living body. This system is the same as the one shown in FIG. 1, except for the configuration of the shaft cover 170. Referring to FIG. 16, the shaft cover 170 includes a distal section 75, a proximal section 77 and an intermediately located bent section 79 positioned between the distal section 75 and the proximal section 77. In the illustrated embodiment, the distal section 75 and the proximal section 77 are linearly extending (straight) sections. The intermediately located bent section 79 is bounded on opposite ends by respective bends 79'. The distal section 75 extends from the distal end of the shaft cover 170 to the intermediately located bent section 79, and the proximal section 77 extends from the proximal end 73 of the shaft cover 170 to the intermediately located bent section 79. The bent section 79 is a stiff bent section, meaning that if the bent section 79 is not surrounded by or influenced by a rigid lumen, the bent section 79 is always bent, by virtue of the bends 79', relative to the proximal section 77 and the distal section 75. That is, in the absence of a force or load (external or internal) applied to the bent section, the bent section 79 remains bent. On the other hand, when the bent section 79 is inserted into or positioned in the instrument channel 42 of the endoscope 40 (ureteroscope), a force or load is applied to the bent section 79 by the straight instrument channel 42 and so the shape of the section 79 is changed from bent toward straight (i.e., the bent section 79 is somewhat straightened out). When the bent section 79 located in the instrument channel 42 of the ureteroscope is pulled out of the instrument channel 42, the bent section 79 automatically returns to its bent configuration. This configuration of the shaft cover can be used together with any of the operational procedures described above and shown in FIGS. 7-15D as a way of further altering the shape of the retrieving device 30 in a way that facilitates navigation of the suction head into narrow entrances and through sharply curved regions of the living body in order to gain access to a target site (lower calix).

The description above explains that the shaft cover can take a variety of forms. By way of example the shaft cover can be a re-shapeable tube 70 such as shown by way of example in FIGS. 7-9), a shape-memory tube 70' such as depicted by way of example in FIGS. 10 and 12, a coil-fused tube 70" such as illustrated by way of example in FIG. 13), and an accordion-shaped tube 70''' such as shown by way of example in FIG. 14.

In each of the embodiments described above, it is possible to provide an indicator, viewable by the viewing system (objective lens or camera 48) of the endoscope 40, which identifies a change in the angular orientation of the suction head from the first angular orientation to the second angular orientation. The indicator can be provided at a proximal surface area of the device (suction head). The dotted outline 53 in FIG. 1 generally illustrates the proximal surface area of the suction head. As an example, the indicator can be provided at the bottom surface 55 of the suction head 50. The indicator can be one of the following: color, shape, convex/concave, reflection, letter and arrow.

Figure 17A:
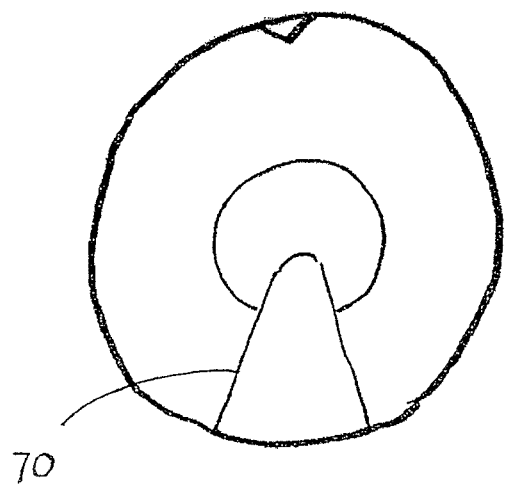
FIGS. 17A and 17B illustrate the bottom of the suction head shown in FIG. 1 as seen from the endoscope (ureteroscope), illustrating one example of an indicator to indicate that the orientation of the suction has changed.
Figure 17B:
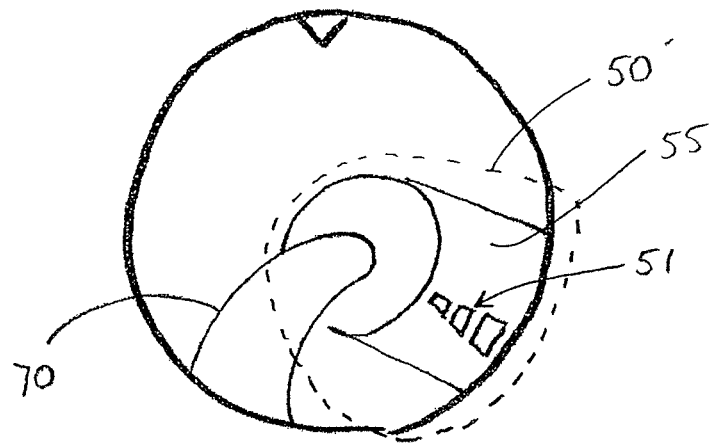

FIGS. 17A and 17B illustrate one way in which this indicator can be implemented and used. FIGS. 17A and 17B illustrate the proximal surface area 53 of the suction head 50 as seen from the viewing system 48 (objective lens or camera) of the endoscope 40. In other words, FIGS. 17A and 17B illustrate the view that would be seen from the endoscope's viewing system 48. As seen in FIG. 17B, the proximal surface area 53 of the suction head 50 is provided with an indicator 51. In this example, the indicator 51 is a color indicator (colored mark(s)). When the shaft cover 70 is generally straight (not significantly bent or curved), the indicator 51 (colored mark(s)) is not visible to the endoscope's viewing system 48. On the other hand, when the shaft cover 70 is bent or curved, the indicator 51 is visible by the endoscope's viewing system 48. It is thus possible to determine that the shaft cover 70 is bent or curved (i.e., the orientation of the suction head 50 is changed) by viewing the proximal surface area of the suction head to identify the indicator 51. As mentioned above, the indicator can take a variety of forms such as those mentioned above and is not limited to an indicator in the form of a colored mark(s).

The detailed description above describes devices and methods for retrieving calculus from parts of a living body such as the ureter and the renal pelvis. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of moving a device toward a target site in a living body, the method comprising:
   introducing an endoscope into the living body, the endoscope possessing a distal end and an instrument channel extending along a longitudinal extent of the endoscope and opening adjacent the distal end of the endoscope, and a device located at the distal end of the endoscope, with an elongated shaft connected to the device and positioned in the instrument channel, the device and the endoscope being movable together, and the introduction of the endoscope into the living body also introducing the device into the living body;
   moving the endoscope and the device within the living body toward the target site;
   changing a shape of the elongated shaft while moving the device in the living body so that an angular orientation of the device relative to a distal end of the elongated shaft changes from a first angular orientation to a second angular orientation, the second angular orientation being different from the first angular orientation, and maintaining a shape of the elongated shaft unless an external force is applied to the elongated shaft; and
   moving the device within the living body toward the target site while the device is in the second angular orientation to position the device at the target site.

2. The method according to claim 1, wherein the device in the living body is moved in a direction of insertion toward the target site, and the changing of the shape of the elongated shaft comprising moving the device and the elongated shaft in the living body so that the device contacts a wall of the living body, and continuing to move the device in the insertion direction toward the target site while the device is in contact with the wall so that the elongated shaft bends to position the device in the second angular orientation, and viewing an indicator at a proximal surface of the device to identify a change from the first angular orientation to the second angular orientation, the indicator being viewed by a viewing system in the endoscope.

3. The method according to claim 2, wherein the proximal surface includes an outer bottom face of the device.

4. The method according to claim 2, wherein the indicator shows a difference between the first angular orientation and the second angular orientation so that the changing of the shape of the elongated shaft is confirmable.

5. The method according to claim 4, wherein the target site is a lower calix in a kidney of the living body, and the wall that is contacted by the device is a wall of a lumen of the kidney.

6. The method according to claim 2, wherein the target site is a lower calix in a kidney of the living body, and the wall that is contacted by the device is a wall of a lumen of the kidney.

7. The method according to claim 1, wherein the device in the living body is moved in a direction of insertion toward the target site, and the changing of the shape of the elongated shaft comprising moving the device in the living body so that the device contacts a wall in the living body, and deflecting the endoscope in a direction different from the insertion direction while the device is in contact with the wall of the body tissue so that the elongated shaft bends to position the device in the second angular orientation, and viewing an indicator at a proximal portion of the device to identify a change from the first angular orientation to the second angular orientation, the indicator being viewed by a viewing system in the endoscope.

8. The method according to claim 1, wherein the changing of the shape of the elongated shaft comprises bending the instrument channel together with the elongated shaft while the device and the endoscope are in the living body to bend the shaft into a bent configuration and cause the shaft to retain the bent configuration as the device is moved in the living body toward the target site.

9. The method according to claim 1, wherein the changing of the shape of the elongated shaft comprises maintaining a bending of the instrument channel together with the elongated shaft while the device and the endoscope are in the living body to bend the shaft into a bent configuration and cause the shaft to retain the bent configuration as the device is moved in the living body toward the target site.

10. The method according to claim 1, wherein the device is a suction head that sucks calculus into the suction head.

11. The method according to claim 1, wherein the target site is a lower calix in a kidney of the living body.

12. A method of moving a device toward a target site in a living body, the method comprising:
   changing a shape of an elongated shaft connected to a device, the device being located at a distal end of an endoscope, the endoscope including an instrument channel extending along a longitudinal extent of the endoscope and opening adjacent the distal end of the endoscope, the elongated shaft being positioned in the instrument channel, the shape of the elongated shaft being changed from a first shape to a second bent shape by applying a force that changes the shape of the elongated shaft, the elongated shaft maintaining the second shape after removing the force;
   introducing the endoscope together with the elongated shaft and the device into a lumen in the living body, the introducing causing the elongated shaft in the second bent shape to straighten from the second bent shape toward the first shape;

moving the endoscope together with the elongated shaft and the device along the lumen in the living body toward the target site;

restoring the elongated shaft toward the second bent shape when the elongated shaft reaches an enlarged region in the living body;

viewing an indicator at a proximal surface of the device to identify a change from the first shape to the second bent shape, the indicator being viewed by a viewing system in the endoscope;

moving the device and the elongated shaft which has been restored toward its second bent shape in an insertion direction toward the target site; and positioning the endoscope together with the device and the elongated shaft which has been restored toward its second bent shape at the target site.

13. The method according to claim 12, wherein the proximal surface includes an outer bottom face of the device.

14. The method according to claim 12, wherein the target site is a lower calix in a kidney of the living body.

15. The method according to claim 12, wherein the introducing of the endoscope together with the elongated shaft and the device into the lumen in the living body includes introducing the endoscope together with the elongated shaft and the device into a ureteral access sheath in the living body.

16. The method according to claim 12, wherein the endoscope is an ureteroscope.

17. The method according to claim 12, wherein the enlarged region in the living body is a renal pelvis in the living body.

18. The method according to claim 12, further comprising, following the restoring of the elongated shaft toward the second bent shape when the elongated shaft reaches an enlarged region in the living body, moving the device in the living body so that the device contacts a wall in the living body, and continuing to move the device in the insertion direction toward the target site while the device is in contact with the wall so that the elongated shaft which has been restored toward its second bent shape is further bent.

19. The method according to claim 12, further comprising, following the restoring of the elongated shaft toward the second bent shape when the elongated shaft reaches an enlarged region in the living body, moving the device in the living body so that the device contacts a wall in the living body, and moving the device in a direction different from the insertion direction while the device is in contact with the wall of the body tissue so that the elongated shaft which has been restored toward its second bent shape is further bent.

20. A method of moving a device toward a target site in a living body, the method comprising:

introducing an endoscope into the living body, the endoscope possessing a distal end and an instrument channel extending along a longitudinal extent of the endoscope and opening adjacent the distal end of the endoscope, and a device located at the distal end of the endoscope and possessing a central axis, with an elongated shaft possessing a distal end portion connected to the device and positioned in the instrument channel, the device being rotatable about a hinge, the device and the endoscope being movable together, and the introduction of the endoscope into the living body also introducing the device into the living body;

moving the endoscope and the device within the living body toward the target site;

rotating the device about the hinge to change an angular orientation of the device relative to the shaft from a first angular orientation in which an angle between the central axis of the distal end portion of the elongated shaft and the central axis of the device is a first angle to a second angular orientation in which the angle between the central axis of the distal end portion of the elongated shaft and the central axis of the device is a second angle that is different from the first angle; and moving the device within the living body while the device is in the second angular orientation to position the device at the target site.

* * * * *